(12) United States Patent
Huang

(10) Patent No.: US 11,839,568 B2
(45) Date of Patent: Dec. 12, 2023

(54) ORTHODONTIC APPLIANCE AND ITS MANUFACTURING METHOD THEREOF

(71) Applicant: Chi-Ching Huang, Taoyuan (TW)

(72) Inventor: Chi-Ching Huang, Taoyuan (TW)

( * ) Notice: Subject to any disclaimer, the term of this patent is extended or adjusted under 35 U.S.C. 154(b) by 147 days.

(21) Appl. No.: 17/367,462

(22) Filed: Jul. 5, 2021

(65) Prior Publication Data
US 2022/0000656 A1 Jan. 6, 2022

(30) Foreign Application Priority Data
Jul. 6, 2020 (CN) .......................... 202010641369.6

(51) Int. Cl.
*G06T 15/00* (2011.01)
*A61F 5/56* (2006.01)
*A61C 7/08* (2006.01)
*A61C 7/00* (2006.01)

(52) U.S. Cl.
CPC ............... *A61F 5/566* (2013.01); *A61C 7/08* (2013.01); *A61C 7/002* (2013.01)

(58) Field of Classification Search
CPC .. A61C 7/08; A61C 5/566; A61C 5/56; A61C 7/36; A61C 7/002
USPC ............................................. 345/418
See application file for complete search history.

(56) References Cited

U.S. PATENT DOCUMENTS

| | | | | |
|---|---|---|---|---|
| 11,622,836 B2* | 4/2023 | Shojaei | ................ | G16H 20/30 345/419 |
| 11,678,954 B2* | 6/2023 | Wu | ........................ | G06F 30/00 703/11 |
| 2009/0113714 A1* | 5/2009 | Greenberg | .............. | B21F 43/00 29/896.11 |
| 2014/0120488 A1* | 5/2014 | Greenberg | ............. | A61C 7/002 433/6 |
| 2021/0315669 A1* | 10/2021 | Huang | ................... | A61C 7/282 |
| 2021/0315729 A1* | 10/2021 | Huang | .................... | A61F 5/566 |
| 2022/0000656 A1* | 1/2022 | Huang | ...................... | A61C 7/08 |
| 2022/0361984 A1* | 11/2022 | Philip | ....................... | A61C 5/30 |
| 2023/0035538 A1* | 2/2023 | Marshall | .............. | A61C 9/0053 |

OTHER PUBLICATIONS

Ackerman JL, Proffit WR, Sarver DM, Ackerman MB, Kean MR. Pitch, roll, and yaw: describing the spatial orientation of dentofacial traits. American Journal of Orthodontics and Dentofacial Orthopedics. Mar. 1, 2007;131(3):305-10.*

(Continued)

*Primary Examiner* — Phu K Nguyen

(57) ABSTRACT

An orthodontic appliance for movably disposed inside dental patient's mouth. The dental patient's mouth has a maxillary dental arch, a mandibular dental arch, and defines a lingual side, a labial side, and a buccal side. The orthodontic appliance has a hard maxillary retainer corresponding to patient's upper jaw, a hard mandibular retainer corresponding to patient's lower jaw, and a soft retainer rigidly attached to the hard maxillary retainer and hard mandibular retainer. The hard maxillary retainer and hard mandibular retainer can be prefabricated according to expected Cusp-to-Fossa Relationship of dental patient, and then be manufactured in an injection mold. The orthodontic appliance can have function to treat teeth deviation, dislocation, malocclusion, or teeth unmatch.

3 Claims, 28 Drawing Sheets

(56) References Cited

OTHER PUBLICATIONS

Al-Balaa M, Li H, Mohamed AM, Xia L, Liu W, Chen Y, Omran T, Li S, Hua X. Predicted and actual outcome of anterior intrusion with Invisalign assessed with cone-beam computed tomography. American Journal of Orthodontics and Dentofacial Orthopedics. Mar. 1, 2021;159(3):e275-80.*

Buschang PH, Ross M, Shaw SG, Crosby D, Campbell PM. Predicted and actual end-of-treatment occlusion produced with aligner therapy. The Angle Orthodontist. Aug. 2015;85(5):723-7.*

Kang SH, Kim MK, You TK, Lee JY. Modification of Planned Postoperative Occlusion in Orthognathic Surgery, Based on Computer-Aided Design/Computer-Aided Manufacturing-Engineered Preoperative Surgical Simulation. Journal of Oral and Maxillofacial Surgery. Jan. 1, 2015;73(1):134-51.*

Taneva E, Kusnoto B, Evans CA. 3D scanning, imaging, and printing in orthodontics. Issues in contemporary orthodontics. Sep. 3, 2015;148(5):862-7.*

\* cited by examiner

ORTHODONTIC APPLIANCE AND ITS MANUFACTURING METHOD THEREOF

CROSS-REFERENCE TO RELATED APPLICATION

The present application is based upon and claims priority to Chinese Patent Applications No. 202010641369.6 filed on Jul. 6, 2020, the content of which is hereby incorporated by reference in its entirety.

TECHNICAL FIELD

The present invention relates to a dental orthodontic appliance, and particularly to an orthodontic appliance which can guide jaws occlusion, treat bite muscle, train patient's breath, assist patient's sleep, relieve snoring condition, and even further help realign teeth, reshape dental arch profile, to correct patient's crooked or dislocated teeth.

BACKGROUND

So many people have problem of snoring, sleeping interruption or mouth breathing while sleeping, but they normally pay minimal attention on these issues. Clinically, temporary stoppage of breathing caused from snoring will end up with sleep apnea syndrome. When human respiratory passage is blocked, there is not enough air reaching human's lung, and thus anoxia or hypoxia is occurred, as well as carbon dioxide level within human body begins to rise. Which will lead to human waking up abruptly, accompanying with choking or gasping for air. Afterward, human's respiratory tract reopens, and then the patient is likely to take several deep breaths and falls back to sleep. Soon after, another round of pauses in breathing may follow, and the cycle will repeat itself throughout whole night. This would cause the sleep broken into several pieces. If human have both snoring, mouth-breathing and obstructive sleep apnea, it will cause long term anoxia or hypoxia, therefore the blood vessels become narrower, and then the damage is easily made. Which can bring several health issues such as high blood pressure, fatigue, cardiovascular disease, dysautonomia, and dysglycemia. As time goes by, these problems can cause further and unexpected damages to the heart, kidney, and other organs, while increasing the chances of sudden death. In addition, some people have problem of mouth breathing, which probably results into respiratory allergy, lower resting position of the tongue, adenoids, or hyperplasia of tonsils. At some worst cases, these symptoms could further lead to malfunction of the tongue, difficulty of swallowing, gum disease, teeth dislocation, bone deformities, or nasal septum deviation, etc. All these problems could negatively impact one's sleep quality and physical well-being.

There are several reasons for snoring; the most common one is that: the muscles which originally hold and support the throat relax while sleep, causing the oral muscles to retreat and making the tongue to drop below its normal resting position. Afterward, human's respiratory tract becomes narrower and then air flows faster, making the soft palate, uvula, tongue, and tonsils in a relaxed state to vibrate with big noise. For mouth-breathing, the causes might also include cold, allergy, nasal polyp, and some structural problem such as tongue-tie (ankyloglossia) and other oral or nasal cavity.

In addition to snoring, mouth breathing and sleep apnea, many patients also have dental problems such as teeth deviation, dislocation, malocclusion, teeth unmatch, etc. These problems are normally treated through dentition correction to make the dental patient's teeth gradually move and rotate, and adjust to the correct occlusal position, and to achieve the Class I tooth relationship of Angle's Classification. And eventually, the bones of the upper jaw and lower jaw will gradually move to the corresponding Centric Relation (CR).

To achieve the improvement of snoring, mouth breathing and sleep apnea, as well as orthodontic treatment of tooth deviation and malocclusion, we usually need to carry out symptomatic treatment through two different departments. Because of the inefficiency, the time of treatment for patients is prolonged and the cost of treatment is increased, which absolutely brings huge unsatisfactory.

Therefore, how to correct snoring, mouth breathing, sleep apnea, teeth unmatch and malocclusion in a single dental treatment is truly urgent to those skilled in the art.

SUMMARY

The primary objective of the present invention are to reduce or eliminate the snoring and sleep apnea caused by dysfunctional breath, and let the patients with sleep apnea or severe snoring carry out "breath training", so as to recover his/her nasal respiratory function. In this manner, improvement of their snoring symptoms and sleep quality, and elimination of the snoring are hence achievable.

Another objective of the present invention are to correct oral muscle function, reshape jaw bones, and carry out dentition adjustment and occlusion adjustment, to achieve orthodontic treatment and malocclusion treatment. Thus patient's teeth are able to be adjusted and moved to proper position, to meet Class I occlusion relationship of Angle's Classification, and the upper jaw and lower jaw can match with Centric Relation (CR). And therefore, stability of occlusion and growth of the teeth are as a result improved.

The other objective of the present invention are to improve and treat the malalignment or malocclusion of teeth, or to achieve alveolar bone shaping and repair by utilizing the biological morphology. Even more, teeth alignment and arrangement can be made, to treat overgrowth or underdevelopment of dental arch; in the meantime, teeth brushing and common oral cleaning work during the orthodontic period do not need to be suspended.

Further objective of the present invention is to make the orthodontic appliance have the function of upper and lower jaw fixation, so that the bite of the maxillary and mandibular dental arch can meet the cusp & fossa relationship.

For dealing with those issues addressed, the present invention suggests an orthodontic appliance for movably disposed inside dental patient's mouth. The dental patient's mouth has a maxillary dental arch, a mandibular dental arch, and defines a lingual side, a labial side, and a buccal side. The orthodontic appliance has a hard maxillary retainer, a hard mandibular retainer, and a soft retainer. The hard maxillary retainer is fitted and detachably engaged with the maxillary dental arch. The hard mandibular retainer is fitted and detachably engaged with the mandibular dental arch. The soft retainer has a median part, a first holding part, a second holding part, a third holding part and a fourth holding part. The first holding part engages with the labial side or the buccal side of the hard maxillary retainer. The second holding part engages with the labial side or the buccal side of the hard mandibular retainer. The third holding part engages with the lingual side of the hard maxillary retainer. The fourth holding part engages with the lingual side of the hard mandibular retainer. The first holding part and the third holding part are located at upper half of the median part, and the second holding part and the fourth holding part are located at lower half of the median part.

According to an embodiment of the aforesaid orthodontic appliance, wherein the soft retainer further has a tongue support extended toward the lingual side orientation and connected to the lingual side of the median part, the third holding part or the fourth holding part. In the further embodiment, altitude of the tongue support is gradually lowered toward the lingual side orientation, or the tongue support is curved-shaped.

According to an embodiment of the aforesaid orthodontic appliance, wherein the soft retainer further has a tongue support extended toward the lingual side orientation and connected to the lingual side of the median part, the third holding part or the fourth holding part. In the further embodiment, the tongue support further has an opening disposed at middle area.

According to an embodiment of the aforesaid orthodontic appliance, wherein the hard maxillary retainer further has a pluralities of customized teeth sites fitted and detachably engaged with patient's teeth of the maxillary dental arch; or the hard mandibular retainer further has a pluralities of customized teeth sites fitted and detachably engaged with patient's teeth of the mandibular dental arch.

According to an embodiment of the aforesaid orthodontic appliance, wherein the hard maxillary retainer further has at least one general tooth site and two customized teeth sites connected to end of the general tooth site, with the customized teeth sites fitted and detachably engaged with patient's first molar of the maxillary dental arch, and the general tooth site accommodated patient's other teeth of the maxillary dental arch.

According to an embodiment of the aforesaid orthodontic appliance, wherein the hard mandibular retainer further has at least one general tooth site and two customized teeth sites connected to end of the general tooth site, with the customized teeth sites fitted and detachably engaged with patient's first molar of the mandibular dental arch, and the general tooth site accommodated patient's other teeth of the mandibular dental arch.

According to an embodiment of the aforesaid orthodontic appliance, wherein the hard maxillary retainer further has a general tooth site accommodated all teeth of the maxillary dental arch; or the hard mandibular retainer further has a general tooth site accommodated all teeth of the mandibular dental arch.

For dealing with those issues addressed, the present invention further suggests a manufacturing method of the orthodontic appliance. The manufacturing method comprises the following steps: Step A01: providing a hard maxillary retainer, a hard mandibular retainer, an upper jaw cast and a lower jaw cast; Step A02: engaging the hard maxillary retainer with the upper jaw cast, and engaging the hard mandibular retainer with the lower jaw cast; Step A03: putting the hard maxillary retainer and the upper jaw cast into an upper cavity of upper die, and putting the hard mandibular retainer and the lower jaw cast into a lower cavity of lower die; Step A05: closing the upper die and the lower die; Step A06: pouring gel into the upper cavity or the lower cavity; Step A07: taking the hard maxillary retainer, the hard mandibular retainer, the upper jaw cast, the lower jaw cast and the hardened gel out of the upper cavity or the lower cavity; Step A08: separating the hard maxillary retainer from the upper jaw cast, and separating the hard mandibular retainer from the lower jaw cast; and Step A10: finishing fabrication of the orthodontic appliance.

According to an embodiment of the manufacturing method of the orthodontic appliance, further comprising Step A04: selectively adjusting positions of the upper die or the lower die toward the lingual side orientation or the labial side orientation.

According to an embodiment of the manufacturing method of the orthodontic appliance, wherein further comprising Step A09: trimming profile of the hardened gel.

According to an embodiment of the manufacturing method of the orthodontic appliance, wherein the fabrication of the hard maxillary retainer or the hard mandibular retainer comprises the following sub-steps: Step B01: oral scanning patient's mouth and obtaining profile of gingiva and teeth; Step B02: accessing spatial information of the gingiva and teeth through a dental software, and setting up a digital model of the gingiva and teeth; Step B03: utilizing the dental software to calculate and simulate the shifting distance or rotating angle of each teeth in each time point of orthodontic process; Step B04: confirming the shifting distance or rotating angle of the teeth in whole orthodontic process, and calculating the profile of the hard maxillary retainer and the hard mandibular retainer; and Step B05: outputting and obtaining physical model of the hard maxillary retainer or hard mandibular retainer.

According to an embodiment of the manufacturing method of the orthodontic appliance, wherein the fabrication of the hard maxillary retainer or the hard mandibular retainer has the following sub-steps: Step C01: obtaining structural profile and 3D spatial information of maxillary teeth and mandibular teeth from a dental patient; Step C02: accessing the 3D spatial information through a dental software, and displaying the structural profile of the maxillary teeth and mandibular teeth; Step C03: recognizing and marking a plurality of fossae of the maxillary teeth and a plurality of cusps of the mandibular teeth; Step C04: connecting the plurality of fossae into an upper occlusion line, and then displaying the upper occlusion line; Step C05: connecting the plurality of cusps into a lower occlusion line, and then displaying the lower occlusion line; Step C06: superimposing the upper occlusion line and the lower occlusion line, and forming an aligning line based on the upper occlusion line and the lower occlusion line; Step C07: arranging a plurality of maxillary correcting positions and a plurality of mandibular correcting positions according to the aligning line; Step C08: setting up profile of the hard maxillary retainer through the maxillary correcting positions, and setting up profile of the hard mandibular retainer through the mandibular correcting positions; and Step C09: outputting and obtaining the physical hard maxillary retainer and hard mandibular retainer.

According to an embodiment of the manufacturing method of the orthodontic appliance, further having the following step: segmentally adjusting profile of the upper occlusion line, lower occlusion line or aligning line toward direction of dental midline.

According to an embodiment of the manufacturing method of the orthodontic appliance, wherein the aligning line is located between the upper occlusion line and the lower occlusion line; or teeth positions of aligning line are located between teeth positions of the upper occlusion line and teeth positions of the lower occlusion line.

For further understanding of the present invention, reference is made to the following detailed description illustrating the embodiments and examples of the present invention.

The description is for illustrative purpose only and is not intended to limit the scope of the claim.

BRIEF DESCRIPTION OF THE DRAWINGS

Preferred embodiments of the invention are shown in the drawings, wherein.

DETAILED DESCRIPTION

The First Embodiment

Figure 1A:
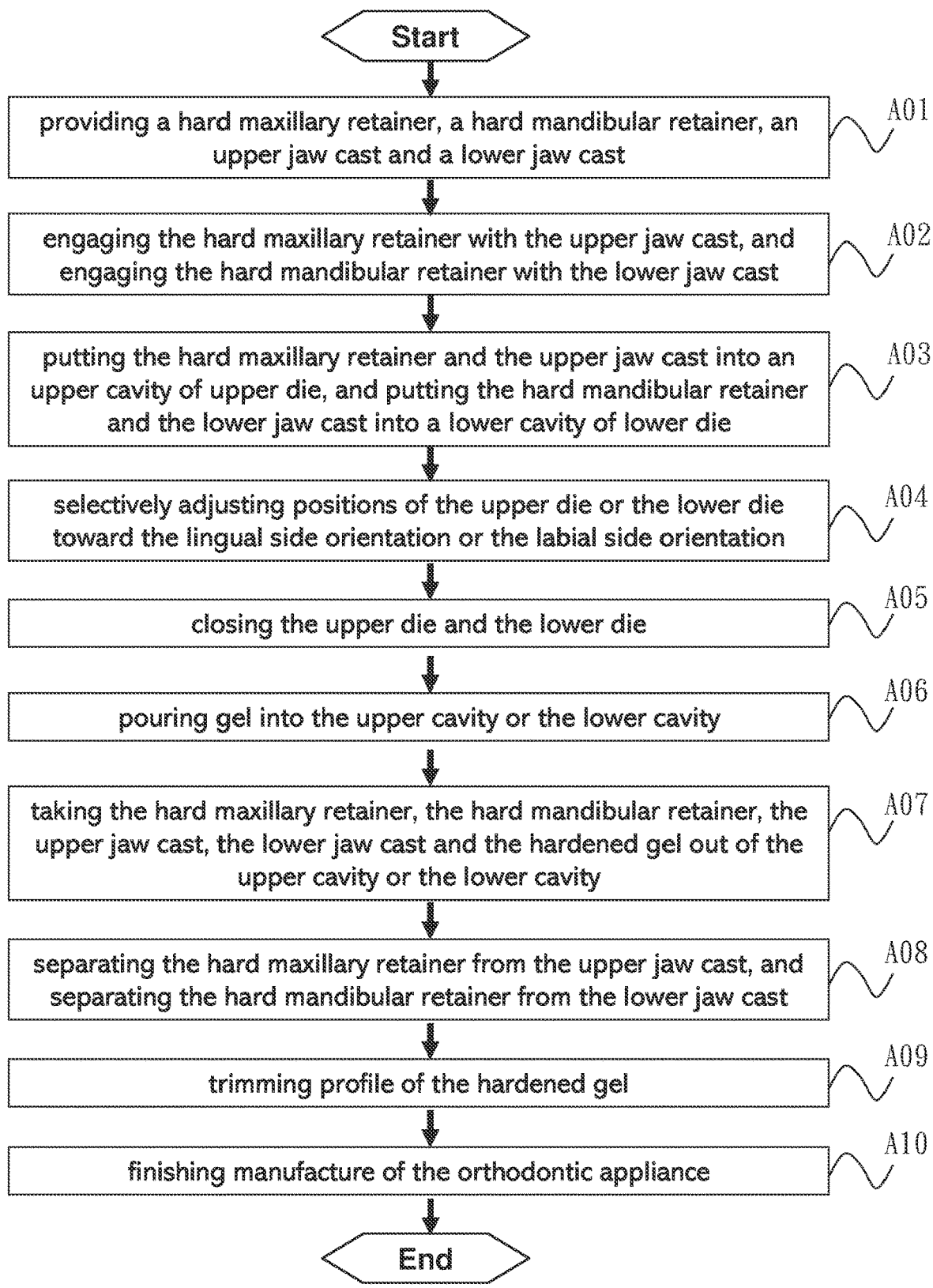
FIG. 1A is flow chart of manufacturing method of the orthodontic appliance in the present invention.
Figure 2A:
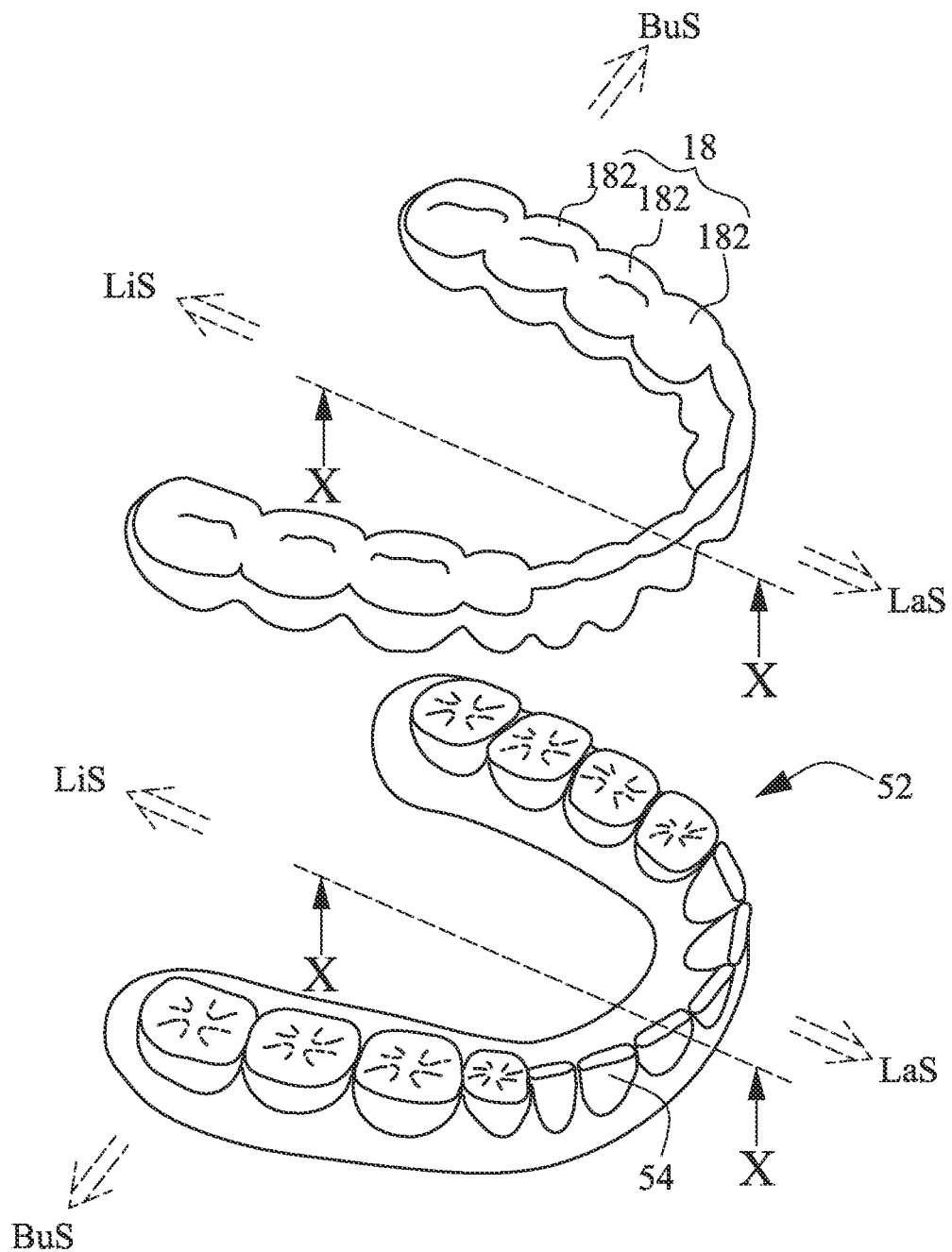
FIG. 2A and FIG. 2B are schematic diagram and X-X sectional diagram of the hard maxillary retainer, hard mandibular retainer, upper jaw cast and lower jaw cast in the first embodiment.

Dental treatment of orthodontics is specific practice for oral cavity, which can have function such as teeth correction, teeth reshape or malocclusion treatment, to achieve perfect teeth alignment and beautiful profile of dental arch. To achieve that goal, the present invention suggests an orthodontic appliance and a manufacturing method to produce the orthodontic appliance. Please refer to FIG. 1A, FIG. 1A is flow chart of manufacturing method of the orthodontic appliance in the present invention. As shown in FIG. 1A, a hard maxillary retainer 17, a hard mandibular retainer 18, an upper jaw cast 51 and a lower jaw cast 52 are provided (Step A01). Please simultaneously refer to FIG. 2A and FIG. 2B, a maxillary dental arch and a mandibular dental arch within a dental patient's mouth (some organs within mouth not depicted) are demonstrated; in this manner, the lingual side LiS orientation is defined in the direction toward tongue of patient; the labial side LaS orientation is defined in the direction toward lips of patient; the buccal side BuS orientation is defined in the direction toward two cheeks of patient. The FIG. 2A shows relative position of the hard mandibular retainer 18 and the low jaw cast 52, and thus the relative position of the hard maxillary retainer 17 and the upper jaw cast 51 is expected. Therefore X-X indicated in FIG. 2A refers to midline of dental arch and demonstrates the cross-sectional view in FIG. 2B. The upper jaw cast 51 and the lower jaw cast 52, respectively duplicating outer profile of the maxillary dental arch and the mandibular dental arch, can be manufactured through plaster reproduced. In some other embodiment, the upper jaw cast 51 and the lower jaw cast 52 can also be produced through oral scanning and 3D printing.

Figure 1B:
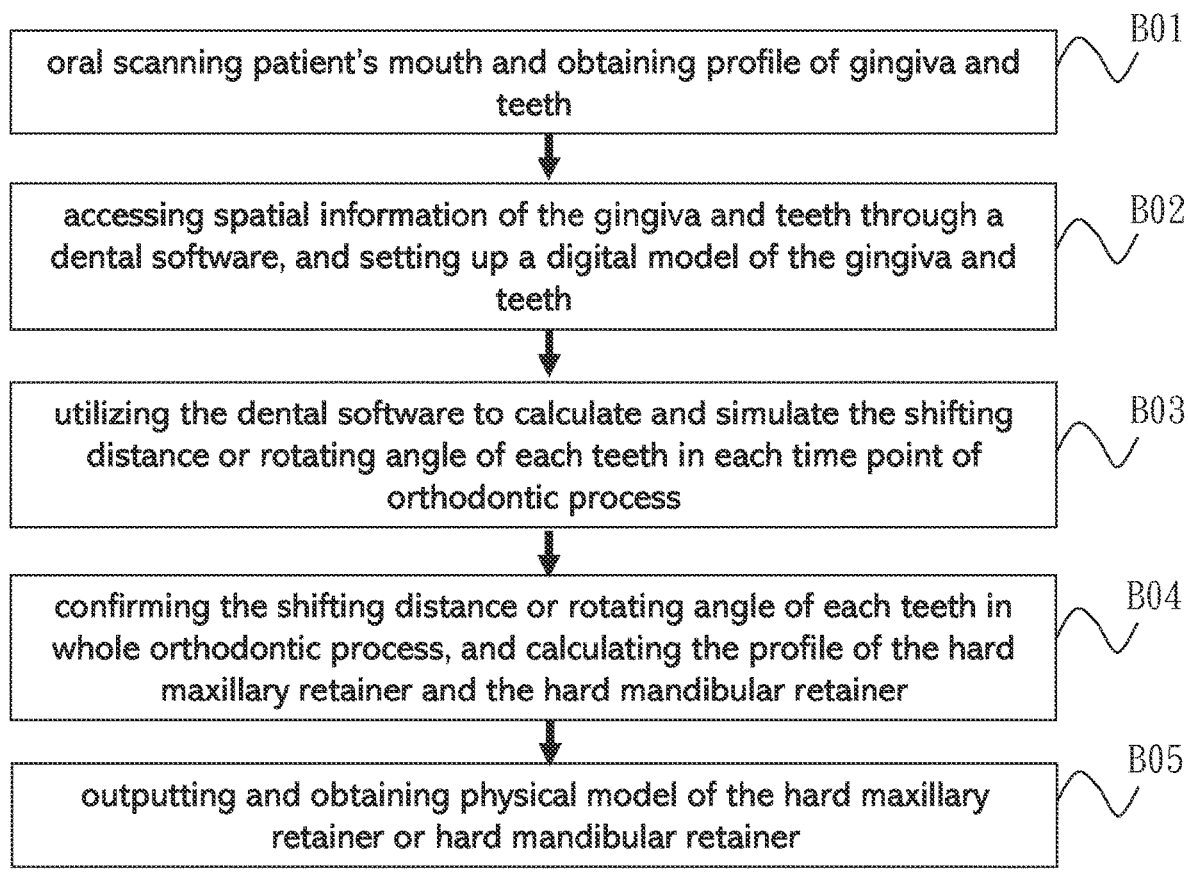
FIG. 1B is flow chart of manufacturing method for hard maxillary retainer and hard mandibular retainer.
Figure 2B:
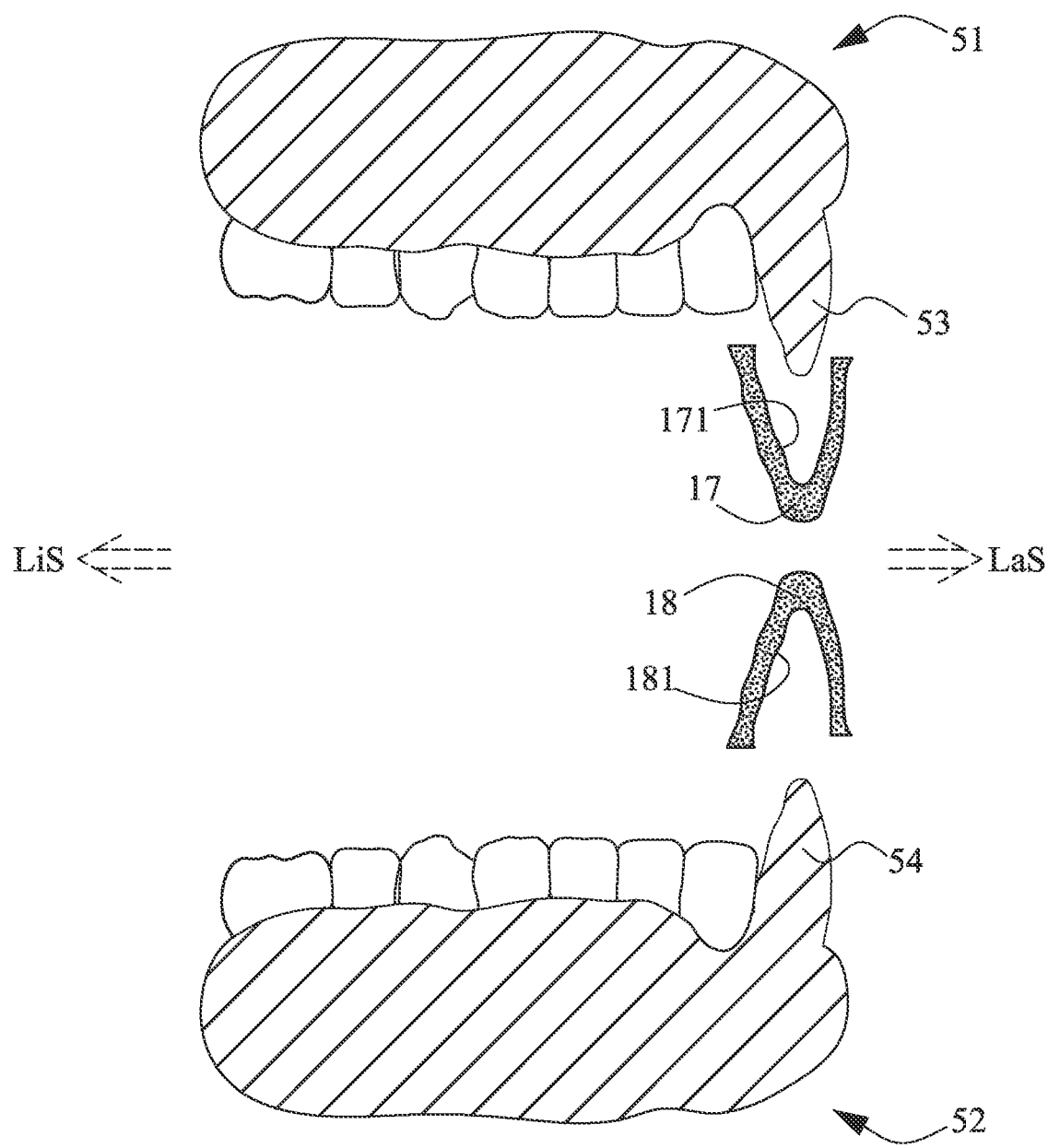

Please refer to FIG. 1B, the hard maxillary retainer 17 and the hard mandibular retainer 18 can be manufactured through the following steps. First, oral scanning patient's mouth and obtaining profile of gingiva and teeth (Step B01), and then accessing spatial information of the gingiva and teeth through a dental software, and setting up a digital model of the gingiva and teeth (Step B02). The spatial information of the gingiva or teeth include but not limited to coordinate or vector of the surface. Next, utilizing the dental software to calculate and simulate the shifting distance or rotating angle of each tooth in each time point of orthodontic process (Step B03). The purpose for simulating the whole orthodontic process in each time point is to detect whether the neighboring teeth interfere or obstruct to each other while the teeth are shifted or rotated. Afterward the dental technician or dentist may check and confirm the shifting distance or rotating angle of each tooth in whole orthodontic process, and thus the profile of the hard maxillary retainer 17 and the hard mandibular retainer 18 are able to be calculated through the dental software (Step B04). In this manner, a physical model of the hard maxillary retainer 17 or hard mandibular retainer 18 is therefore outputted and obtained (Step B05). As shown in FIG. 2A and FIG. 2B, the hard mandibular retainer 18 has a pluralities of customized teeth sites 182, with each customized tooth site 182 detachably engaged with a tooth of the mandibular dental arch of human; therefore, each customized tooth site 182 can correspond to and engage with the tooth of the lower jaw cast 52, since the lower jaw cast 52 is duplicated through mandibular dental arch of dental patient. Similarly, the hard maxillary retainer 17 has a pluralities of customized teeth sites 172 (shown in FIG. 8B and FIG. 8C), with each customized tooth site 172 detachably engaged with a tooth of the maxillary dental arch of human.

The hard maxillary retainer 17 and the hard mandibular retainer 18 can be obtained through dental software controlling and 3D printing. Traditionally the hard maxillary retainer 17 and the hard mandibular retainer 18 are made of polyurethane or some other medical or dental plastic materials, and thus become transparent arch-shaped brackets. In this manner, the hard maxillary retainer 17 and the hard mandibular retainer 18 are thin and flexible to accommodate with maxillary dental arch and mandibular dental arch of a dental patient, without rubbing the gingiva and bringing discomfort to the patient. Due to the transparent material utilized, the hard maxillary retainer 17 and the hard mandibular retainer 18 are commonly known as "invisible braces". The customized teeth sites 172, 182 in the hard maxillary retainer 17 and the hard mandibular retainer 18 are customized and fabricated through duplication of patient's mouth, thus they have the same profile with the teeth of patient. The customized teeth sites 172, 182 are concave shaped, to contain and match with the corresponding teeth of patient. After the maxillary dental arch or the mandibular dental arch of patient are engaged with the hard maxillary retainer 17 or hard mandibular retainer 18, patient's teeth with poor alignment, dislocation, reverse position or crooked teeth conditions can be corrected through the flexible material of the hard maxillary retainer 17 or hard mandibular retainer 18; since their flexible material can bring enough mechanical strength to force patient's teeth rotating, shifting or dental arch expanding. Thus patient's teeth which are not aligned correctly are able to be forced to shift or rotate, and finally enter the correct teeth position. Namely, the patient's teeth can be pushed or drawn, and afterward be located at right positions by means of the customized teeth sites 172, 182; in this manner, the hard maxillary retainer 17 can make the maxillary dental arch arrange in order and align in a beautiful, curved shape. Similarly, the hard mandibular retainer 18 can also make the mandibular dental arch arrange in order and align in a beautiful, curved shape.

The profile of the upper jaw cast 51 is the same as patient's maxillary dental arch and its neighboring gingiva, and the lower jaw cast 52 is the same as patient's mandibular dental arch and its neighboring gingiva; thus the follow-up work of dental technician or dental laboratory, such as dental restoration, denture manufacturing, orthodontic design, can be carried out through the upper jaw cast 51 and the lower jaw cast 52 in dental lab; thus patient does not need to provide real teeth on site. As shown in FIG. 2A and FIG. 2B, the inner side 171 of the hard maxillary retainer 17 has the same contour as the maxillary counterpart 53 of the upper jaw cast 51, thus the inner side 171 can be tightly engaged with the maxillary counterpart 53. The inner side 181 of the hard mandibular retainer 18 has the same contour as the mandibular counterpart 54 of the lower jaw cast 52, thus the inner side 181 can be tightly engaged with the mandibular counterpart 54.

Figure 3A:
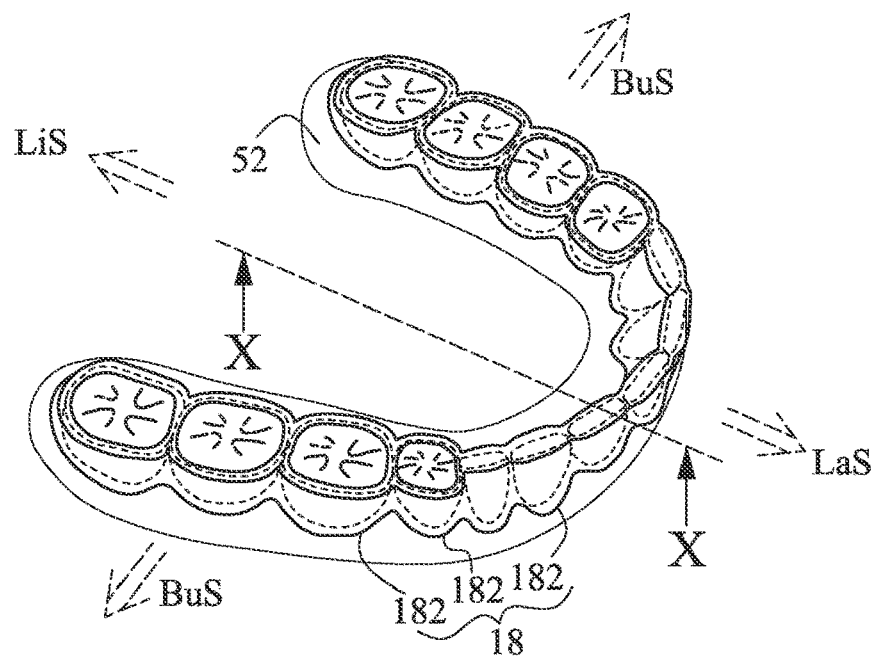
FIG. 3A and FIG. 3B are schematic diagram and X-X sectional diagram demonstrating that the hard maxillary retainer engages with the upper jaw cast and the hard mandibular retainer engages with the lower jaw cast in the first embodiment.
Figure 3B:
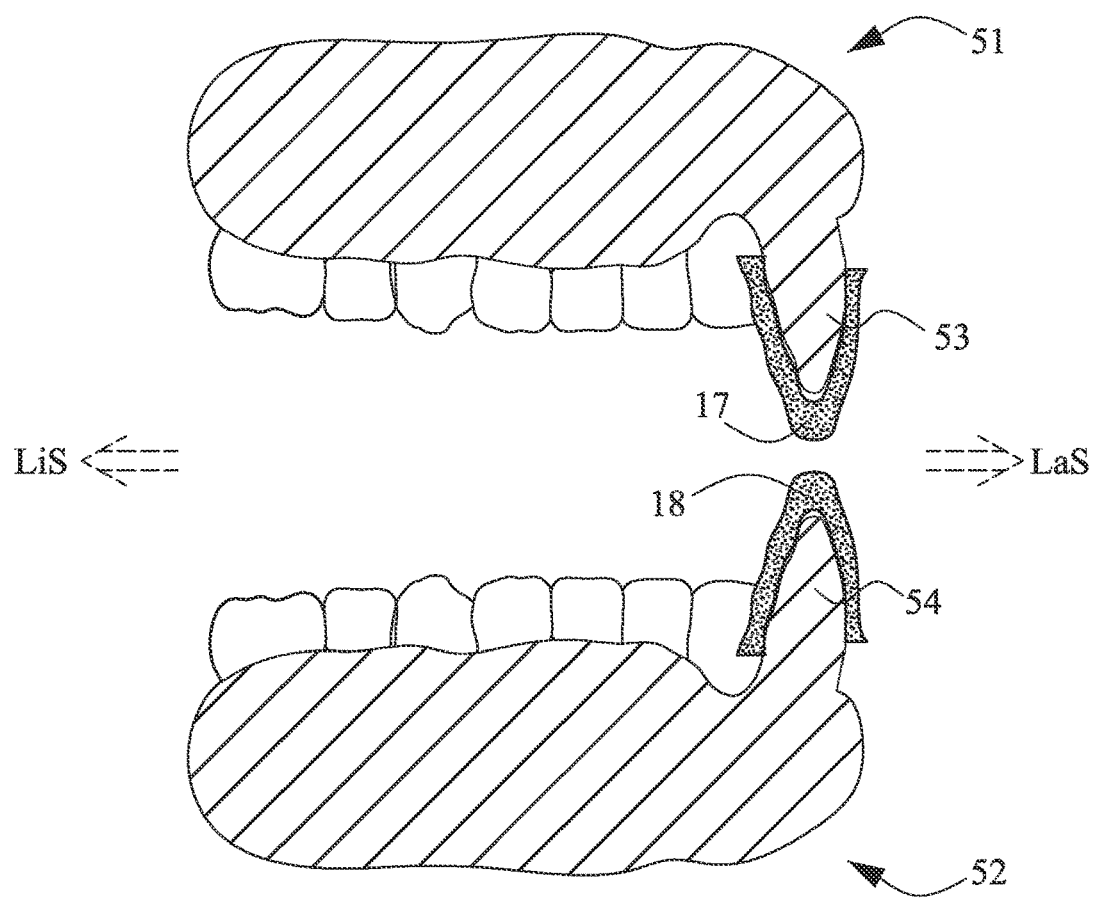

Please refer to FIG. 3A and FIG. 3B, the hard maxillary retainer 17 are approached to and engaged with the upper jaw cast 51, and the hard mandibular retainer 18 are approached to and engaged with the lower jaw cast 52 (Step A02). Due to the identical contours of the inner side 171 and the maxillary counterpart 53, the hard maxillary retainer 17 can be perfectly attached to maxillary counterpart 53 of the upper jaw cast 51, without gap between them. The inner side 181 and the mandibular counterpart 54 have identical contours, therefore the hard mandibular retainer 18 can be perfectly attached to mandibular counterpart 54 of the lower jaw cast 52, without gap between them.

Figure 4A:
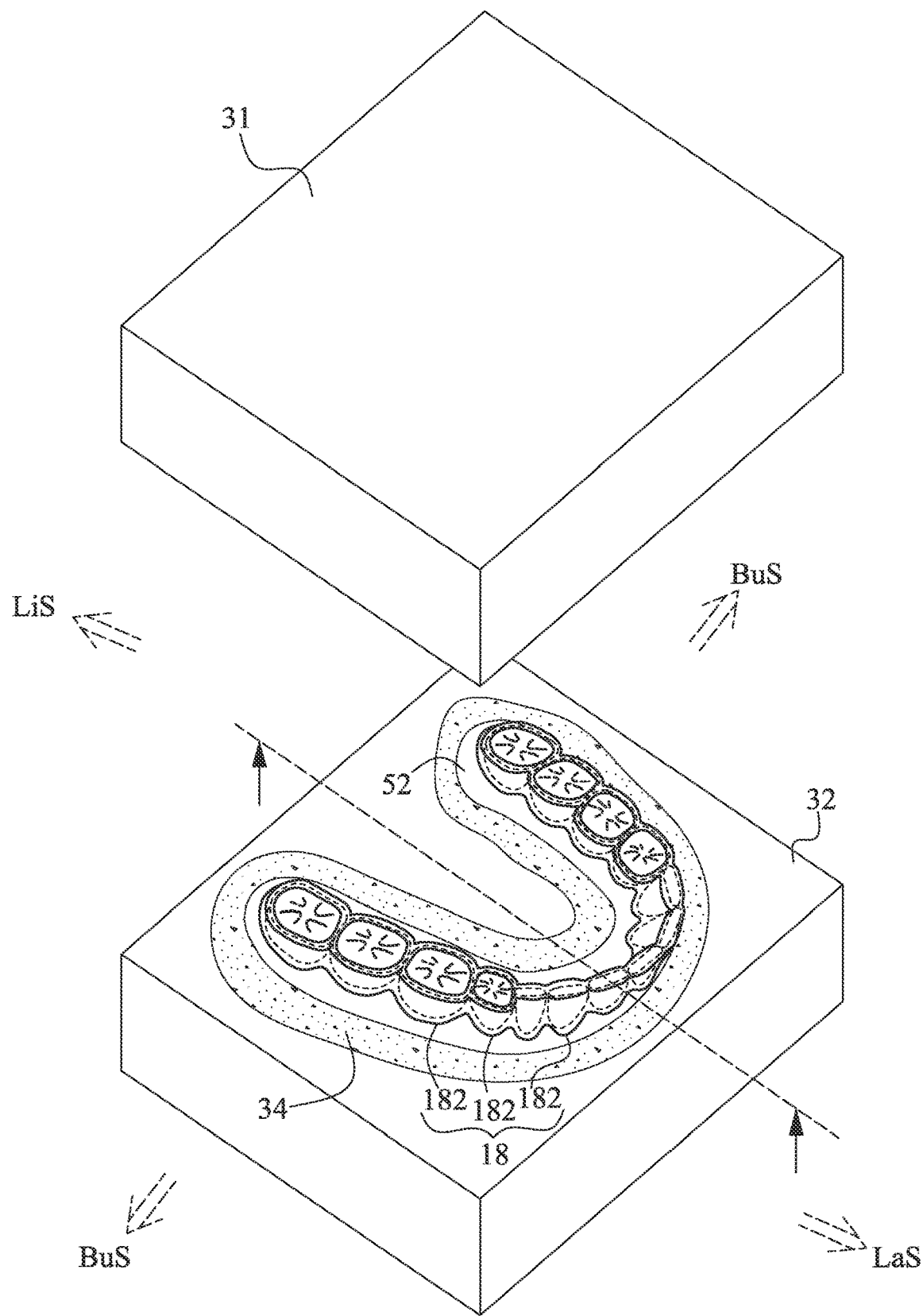
FIG. 4A and FIG. 4B are schematic diagram and X-X sectional diagram demonstrating that the hard maxillary retainer, hard mandibular retainer, upper jaw cast and lower jaw cast are located within the upper die and the lower die.
Figure 4B:
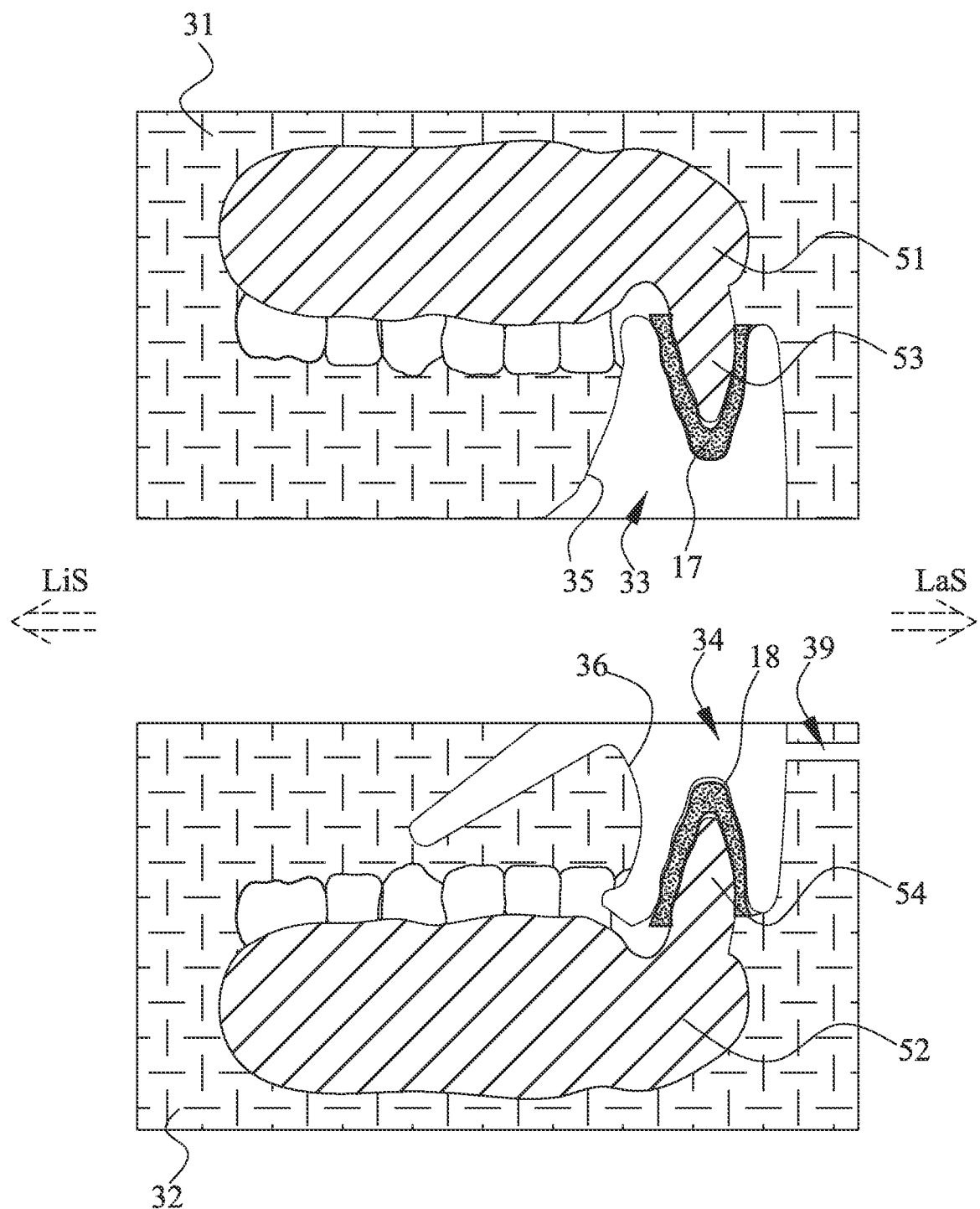
Figure 5:
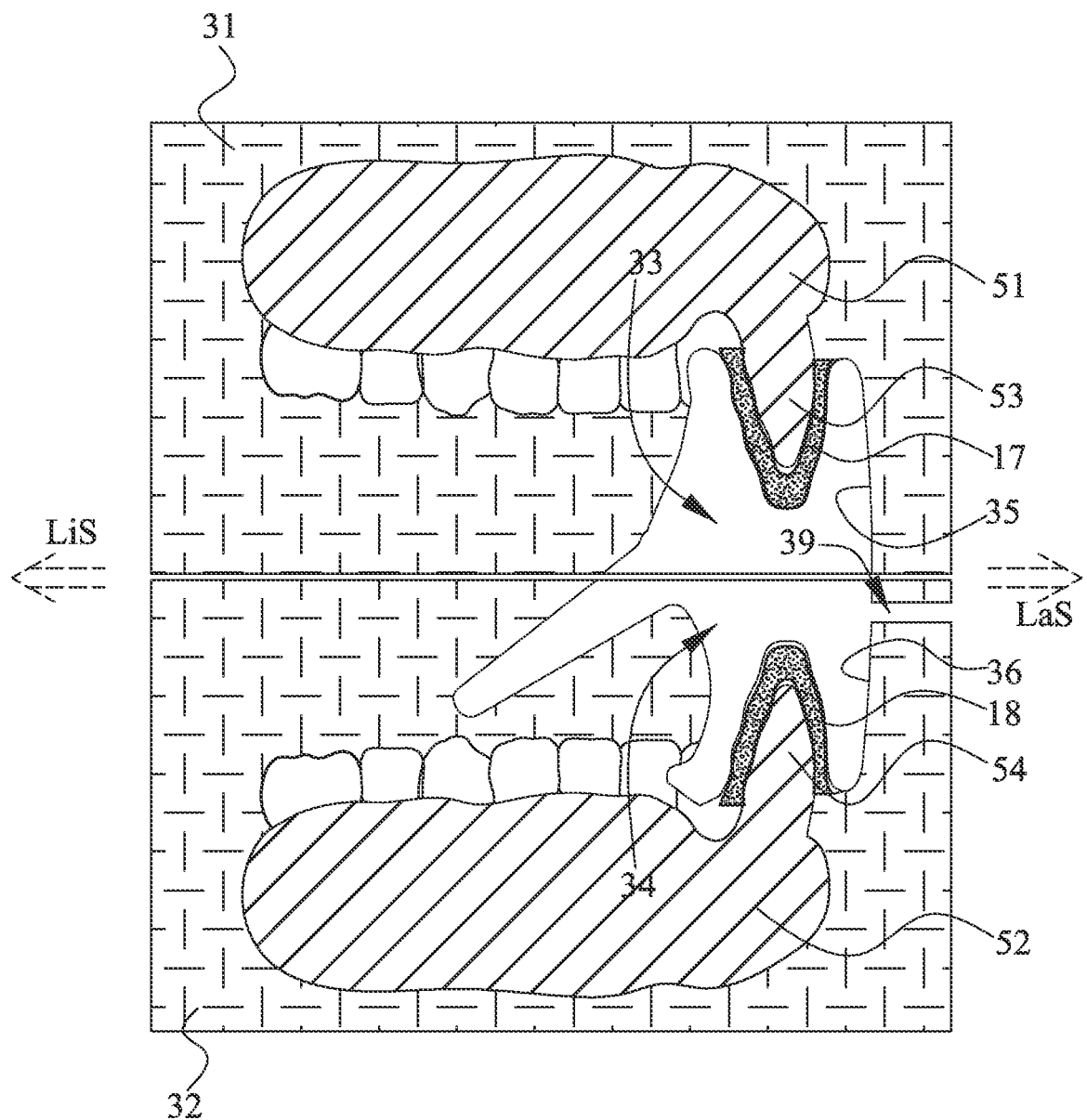
FIG. 5 is diagram demonstrating that the upper die and lower die are closed.

Please refer to FIG. 4A and FIG. 4B, the hard maxillary retainer 17 and the upper jaw cast 51 are putted into the upper cavity 33 of upper die 31, and the hard mandibular retainer 18 and the lower jaw cast 52 are putted into the lower cavity 34 of lower die 32 (Step A03). The upper cavity 33 of the upper die 31 is a space to preserve and accommodate the combined hard maxillary retainer 17 and the upper jaw cast 51. Similarly the lower cavity 34 of the lower die 32 is a space to preserve and accommodate the combined hard mandibular retainer 18 and the lower jaw cast 52. The shape and contour of the upper cavity 33 and the lower cavity 34 will directly determine the final appearance and configuration of the orthodontic appliance 1, therefore the space of the upper cavity 33 and the lower cavity 34 need to be designated according to age of the dental patient or future growth curve of patient's cranial and temporal jaw, so as to reasonably predict the 3D spatial position of each subsequent tooth, and afterward provide the best orthodontic treatment and occlusion correction; since all of these considerations shall certainly involve craniofacial structure, temporomandibular structure and physiological anatomy, etc. As shown in FIG. 4B, after the hard maxillary retainer 17 and the upper jaw cast 51 are disposed within the upper cavity 33, the hard mandibular retainer 18 and the lower jaw cast 52 are disposed within the lower cavity 34, there are still certain spaces in the upper cavity 33 and the lower cavity 34 which are not fully occupied. Then, the positions of the upper die 31 or the lower die 32 can be selectively adjusted toward the lingual side LiS orientation or the labial side LaS orientation (Step A04), thus relative location between the upper jaw cast 51 and the upper die 31, or between the lower jaw cast 52 and the lower die 32 can be regulated and controlled. Afterward the upper die 31 and the lower die 32 are closed (Step A05) as shown in FIG. 5, and the cavity spaces within the upper cavity 33 and the lower cavity 34 will match to each other, so the interior wall 35 and the interior wall 36 will be aligned with each other. The purposes for adjusting the position of the upper die 31 and the lower die 32 in Step A04 are: firstly making the interior wall 35 of the upper cavity 33 match with the interior wall 36 of the lower cavity 34, and secondly making the hard maxillary retainer 17 and the hard mandibular retainer 18 fit and align. So that patient's maxillary dental arch and mandibular dental arch can meet Class I occlusion relationship according to the Angle's Classification and make patient's upper jaw and lower jaw move to Centric Relation (CR), to further improve the stability of occlusion if the patient receives the orthodontic treatment. In this manner, the orthodontic appliance 1 (depicted in FIG. 8A to FIG. 8C) fabricated by means of the steps of present invention may have dental retention function, to correct the maxillary dental arch and mandibular dental arch and achieve perfect Cusp-to-Fossa relationship.

It is noticed that the Angle's Classification classifies occlusion conditions based on human's relative position of the maxillary dental arch and the mandibular dental arch. The Angle's Classification classifies occlusion into 3 types; firstly, Class I: Neutrocclusion. Class I of Angle's Classification means normal occlusion, in which the incisor of upper jaw covers and is anterior to the incisor of the lower jaw by 1 mm to 3 mm Secondly, Class II: Distocclusion. Class II of Angle's Classification means the incisor of upper jaw is too much anterior to the incisor of lower jaw, namely excess overjet or overbite, or compensatory retraction of maxillary incisor leading to skeletal buck teeth. Thirdly, Class III: Mesiocclusion. Class III of Angle's Classification means the incisor of lower jaw is anterior to the incisor of upper jaw, to become negative overjet or anterior crossbite, or have symptoms of maxillary retraction or mandible protrusion (so-called underbite). The position of Centric Occlusion (CO) is the position where the upper teeth and lower teeth bite in the closest-fit condition, namely the upper teeth and lower teeth bite to meet the largest occlusal surface. Furthermore, the Centric Relation (CR) is the mandibular jaw position in which the head of the condyle is situated as far anterior and superior as it possibly can within the mandibular glenoid fossa, where CR is the most stable situation to all teeth. Normally, the most prefect situation is that the position of CO has 0.5 mm to 1 mm displacement away from the position of CR. The orthodontic appliance 1 of the present invention may adjust and correct patient's upper jaw and lower jaw, thus the patient who suffers malocclusion of Class II or Class III occlusion relationship of Angle's Classification can have orthodontic treatment, and then make the patient's maxillary dental arch and mandibular dental arch be gradually moved and rotated, to meet Class I occlusion relationship of Angle's Classification.

Figure 6:
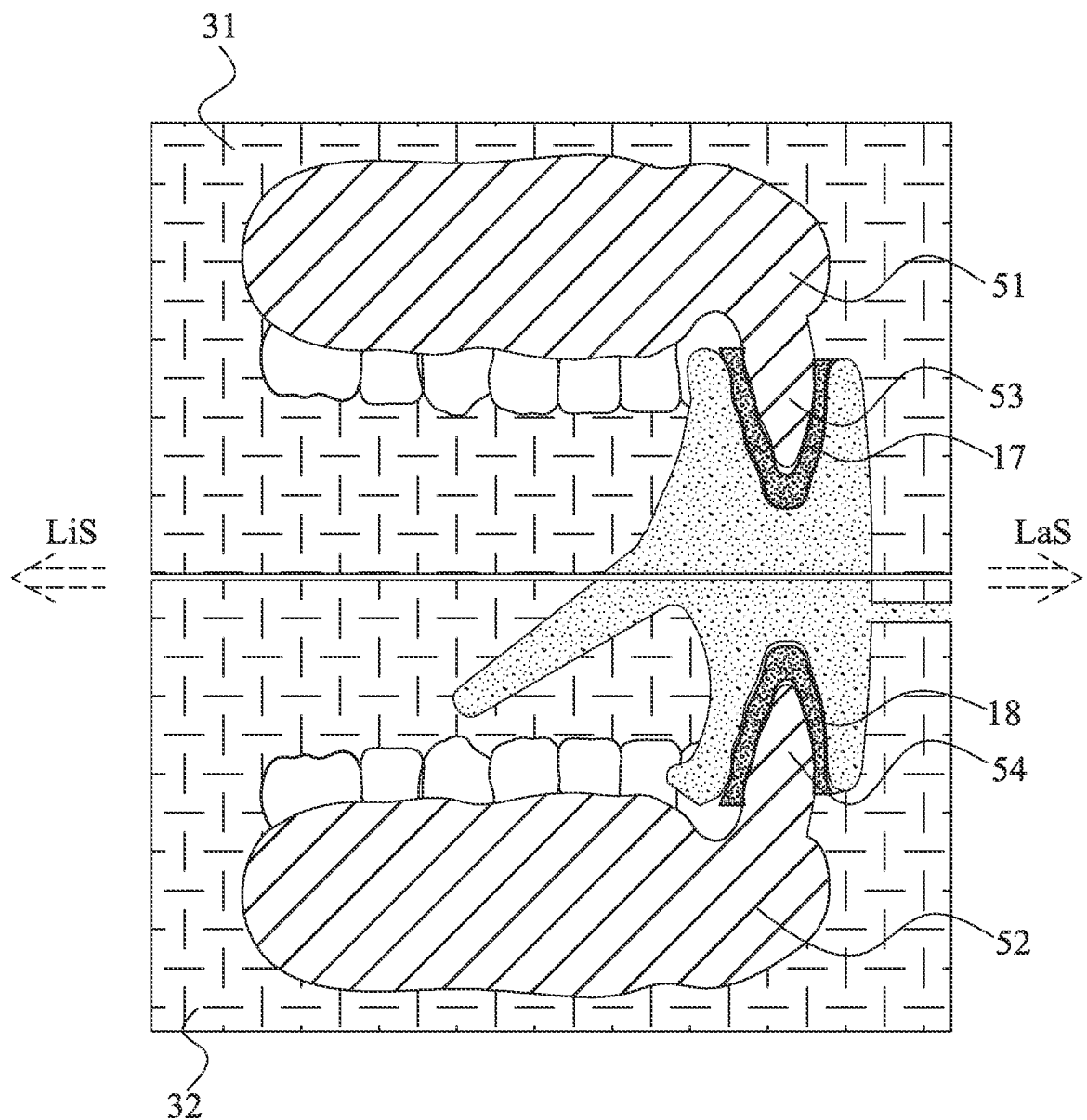
FIG. 6 is diagram demonstrating that silicone is injected to interior of the upper die and the lower die.

Next, as shown in FIG. 6, a dental or medical gel is poured into the upper cavity 33 and the lower cavity 34 (Step A06), so that the gel can enter and occupy the enclosed space of the interior wall 35 and 36. Preferably, the dental or medical gel is made of silicone, and the gel enters the upper cavity 33 and the lower cavity 34 through an injecting channel 39 as shown in FIG. 5, in which the injecting channel 39 is disposed on the lower die 32 to connect the lower cavity 34 and outside of the lower die 32. In other embodiment, the injecting channel 39 can also be disposed on the upper die 31.

Figure 7:
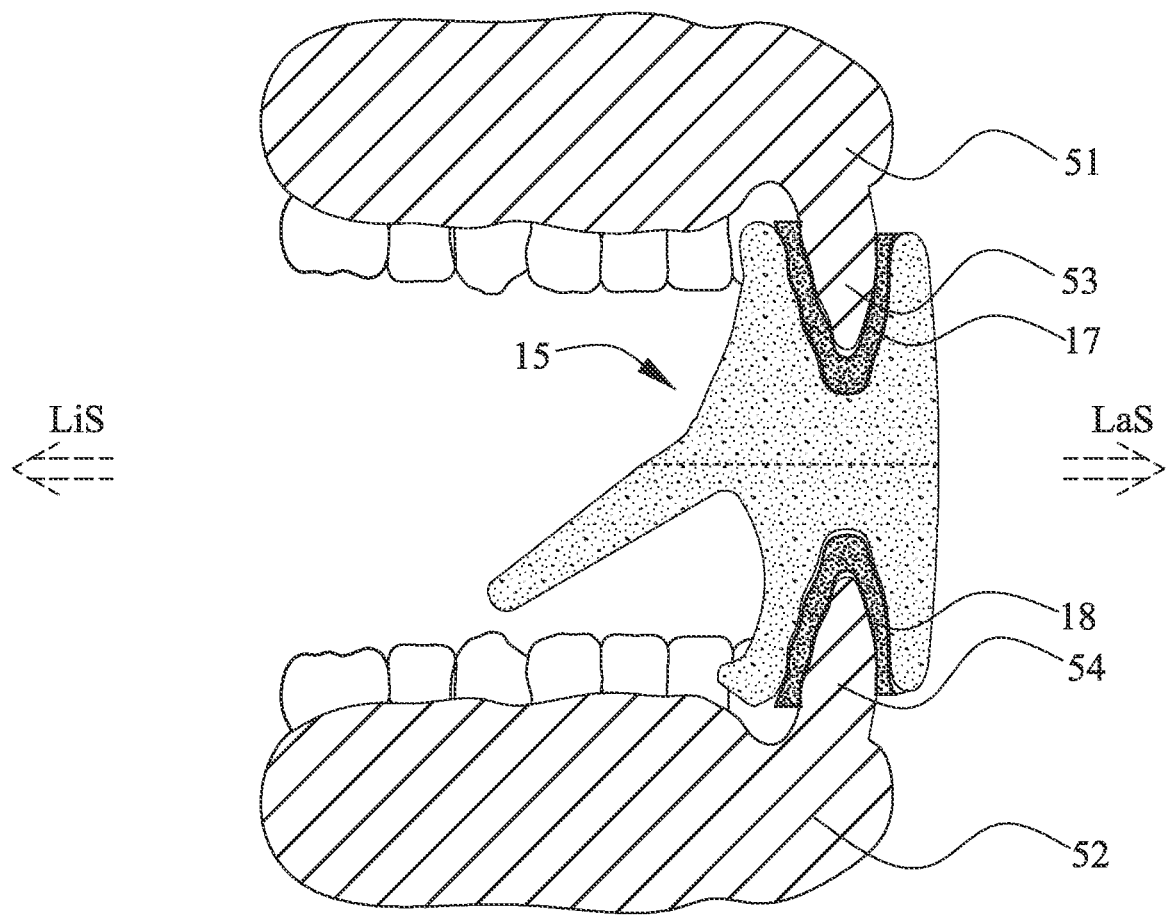
FIG. 7 is diagram demonstrating that the hard maxillary retainer, hard mandibular retainer, upper jaw cast and lower jaw cast are demolded.
Figure 8A:
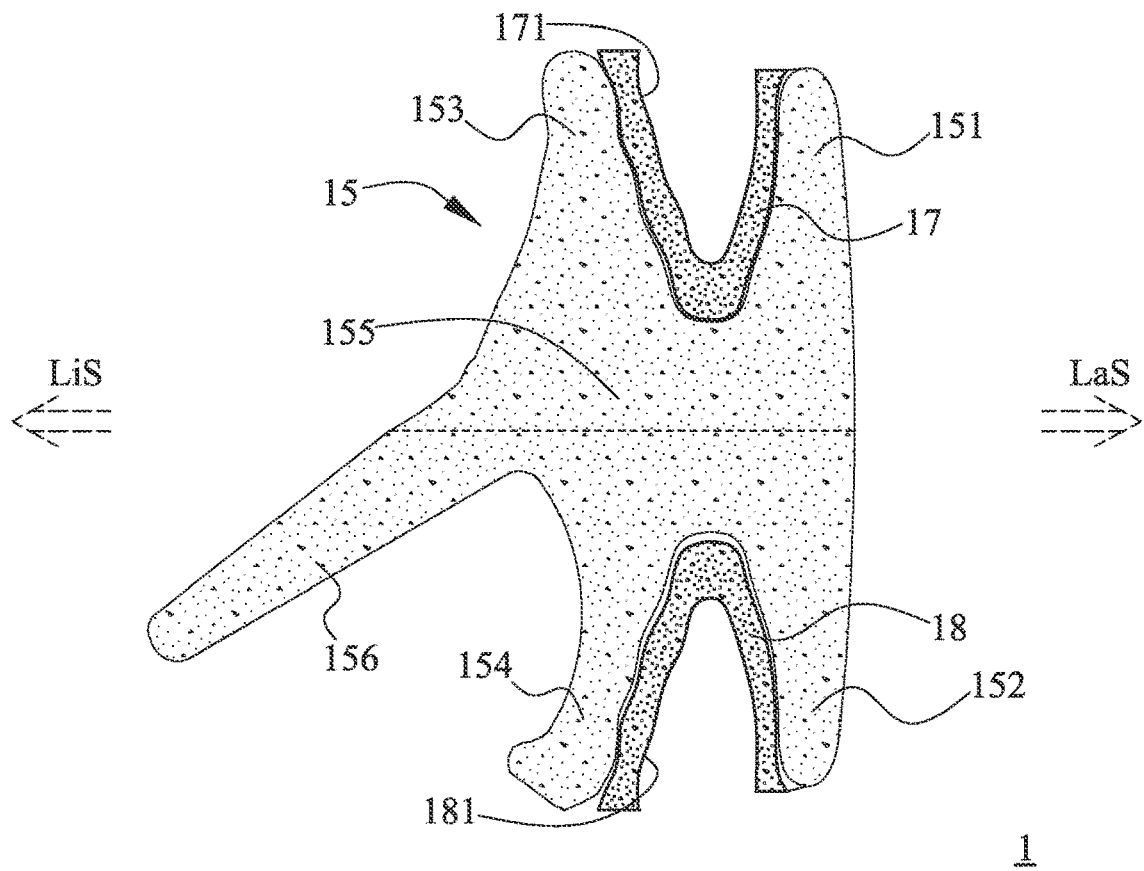
FIG. 8A, FIG. 8B and FIG. 8C are X-X sectional diagram, front view diagram and schematic diagram of the orthodontic appliance of the present invention after it is manufactured.
Figure 8B:
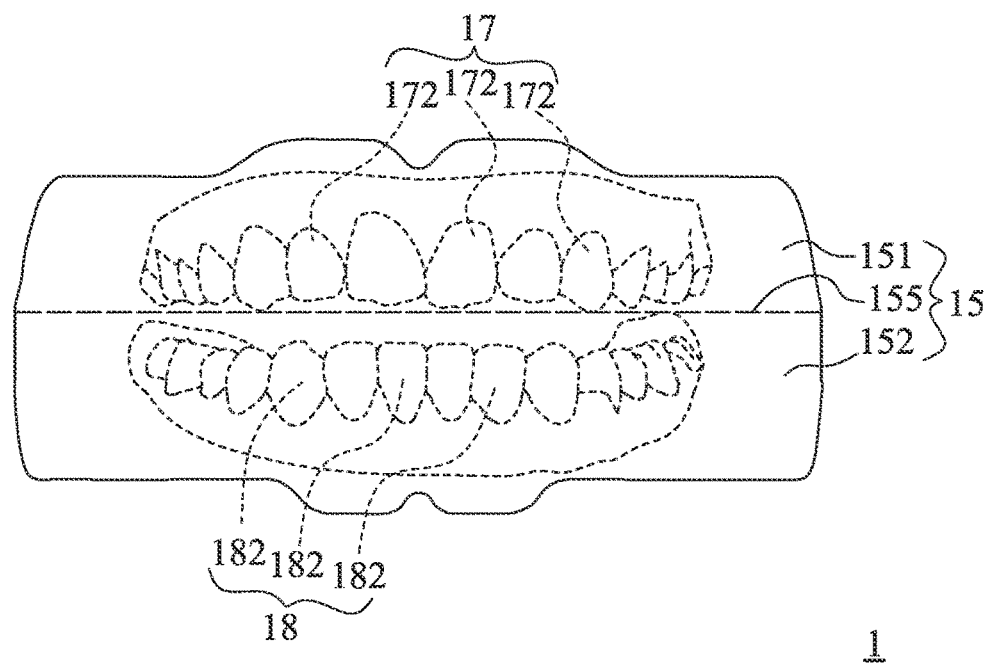
Figure 8C:
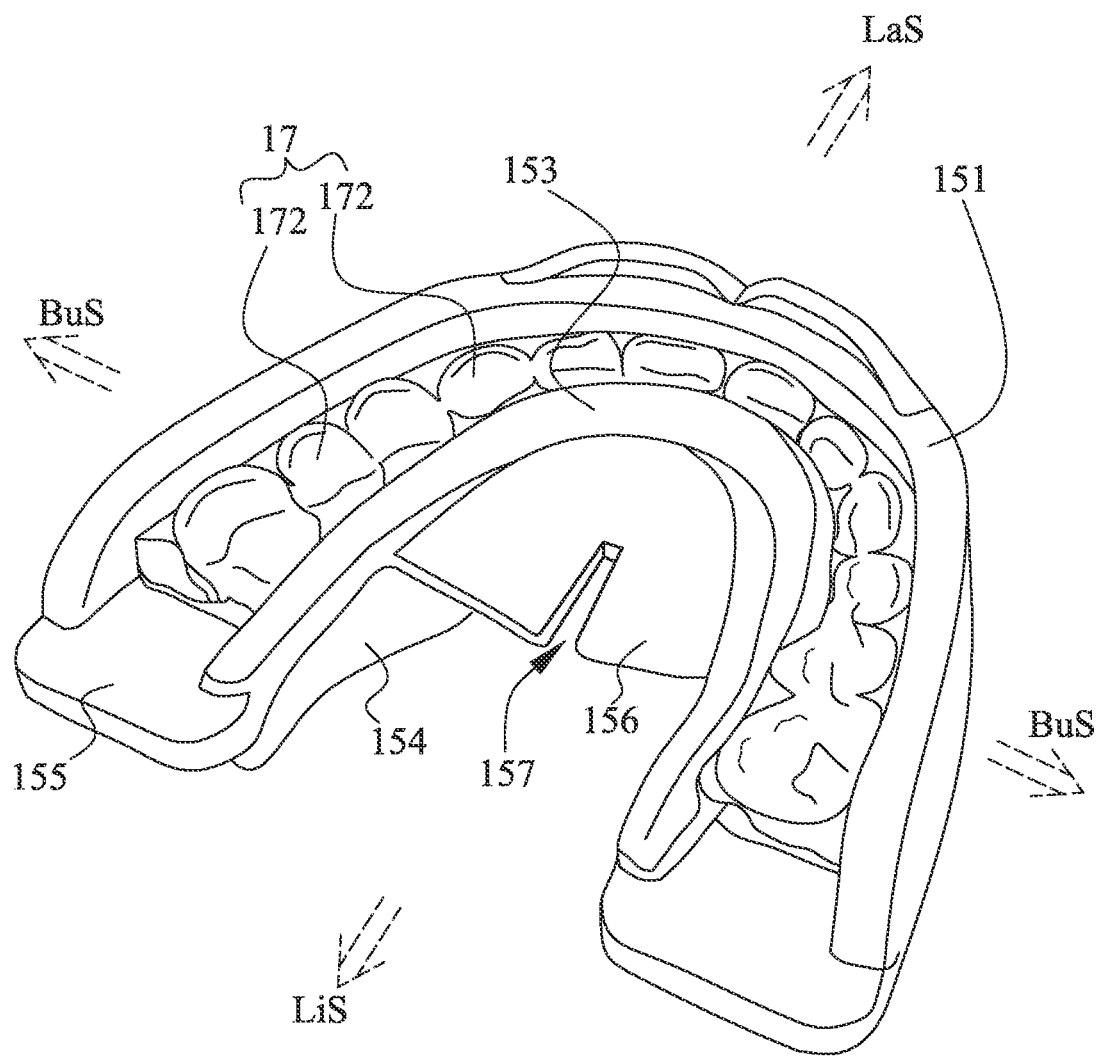

Afterward as shown in FIG. 7, after the gel is hardened, the hard maxillary retainer 17, the hard mandibular retainer 18, the upper jaw cast 51, the lower jaw cast 52 and the hardened gel are taken out of the upper cavity 33 and the lower cavity 34 (Step A07), in which the step is so-called demolding process. Then the hard maxillary retainer 17 is separated from the upper jaw cast 51, and the hard mandibular retainer 18 is separated from the lower jaw cast 52 (Step A08); after separation, as shown in FIG. 8A, FIG. 8B and FIG. 8C, the hardened silica gel can be formed into a soft retainer 15. The soft retainer 15 is combined with the hard maxillary retainer 17 and the hard mandibular retainer 18, to become the orthodontic appliance 1 of the present invention. Due to the injecting molding process, the soft retainer 15 will be rigidly attached to the hard maxillary retainer 17 and the hard mandibular retainer 18, without loosening, separating, or falling off After the orthodontic appliance 1 is produced, the profile of the hardened gel can be selectively trimmed (Step A09), and then fabrication of the orthodontic appliance 1 is fulfilled and finished (Step A10).

When the orthodontic appliance 1 is utilized in orthodontic treatment, the hard maxillary retainer 17 can be disposed around the maxillary dental arch and then tightly engaged with the patient's upper jaw, and the hard mandibular retainer 18 can be disposed around the mandibular dental arch and then tightly engaged with the patient's lower jaw. Namely, patient's maxillary dental arch and mandibular dental arch can bite the orthodontic appliance 1 to receive the orthodontic treatment. In this manner, the technical functions such as teeth eruption guide, occlusion guide, rotating or shifting specific tooth are therefore achieved through the engagement with the hard maxillary retainer 17 and hard mandibular retainer 18. It is noticed that the orthodontic appliance 1 of this embodiment has high potential to treat children in age of 8~12, particularly when the children have teeth crowding, teeth spacing, overbite, overjet, or posterior crossbite, etc. As shown in FIG. 8A~FIG. 8C, the soft retainer 15 of the orthodontic appliance 1 has a median part 155, a tongue support 156, a first holding part 151, a second holding part 152, a third holding part 153 and a fourth holding part 154. The first holding part 151 is engaged with the labial side LaS and the buccal side BuS of the hard maxillary retainer 17. The second holding part 152 is engaged with the labial side LaS and the buccal side BuS of the hard mandibular retainer 18. The third holding part 153 is engaged with the lingual side LiS of the hard maxillary retainer 17. The fourth holding part 154 is engaged with the lingual side LiS of the hard mandibular retainer 18. The first holding part 151 and the third holding part 153 are located at upper half of the median part 155. The second holding part 152 and the fourth holding part 154 are located at lower half of the median part 155. The tongue support 156 of the soft retainer 15 is extended toward the lingual side LiS orientation and connected to the lingual side LiS of the median part 155, the lingual side LiS of the third holding part 153, or the lingual side LiS of the fourth holding part 154. The tongue support 156 can be curved shape, or the upper surface of the tongue support 156 can be a concave, so that the tongue support 156 can support and adapt to lower surface of human's tongue, to effectively eliminate or reduce the uncomfortable feeling of patients and increase the willingness of patients to wear the orthodontic appliance 1. Besides, the altitude of the tongue support 156 is gradually lowered toward the lingual side LiS orientation. When the dental patient bites the orthodontic appliance 1 and puts his/her tongue above the tongue support 156, the muscles in the throat can be relaxed by raising the height of the tongue, and then the respiratory tract can be opened to avoid respiratory obstruction and reduce or eliminate the syndrome of "Mouth Breathing" caused by snoring and low tongue position. Through the setting of the tongue support 156, the soft retainer 15 of the orthodontic appliance 1 in the present invention can enable the patients with sleep apnea or serious snoring problem to carry out "breathing training", to relieve the snoring symptoms, eliminate the snoring sound and frequency, and finally improve the sleep quality.

In the further embodiment as shown in FIG. 8C, the tongue support 156 has an opening 157 disposed at middle area. The opening 157 can be a trough or U-shaped slot. The opening 157 is used to hold the tongue-tie (i.e., ankyloglossia) under the human tongue. In this way, when the patient places the tongue above the tongue support 156, the uncomfortable feeling can be reduced, and the willingness of the dental patient to use can be further increased.

Second Embodiment

Figure 9A:
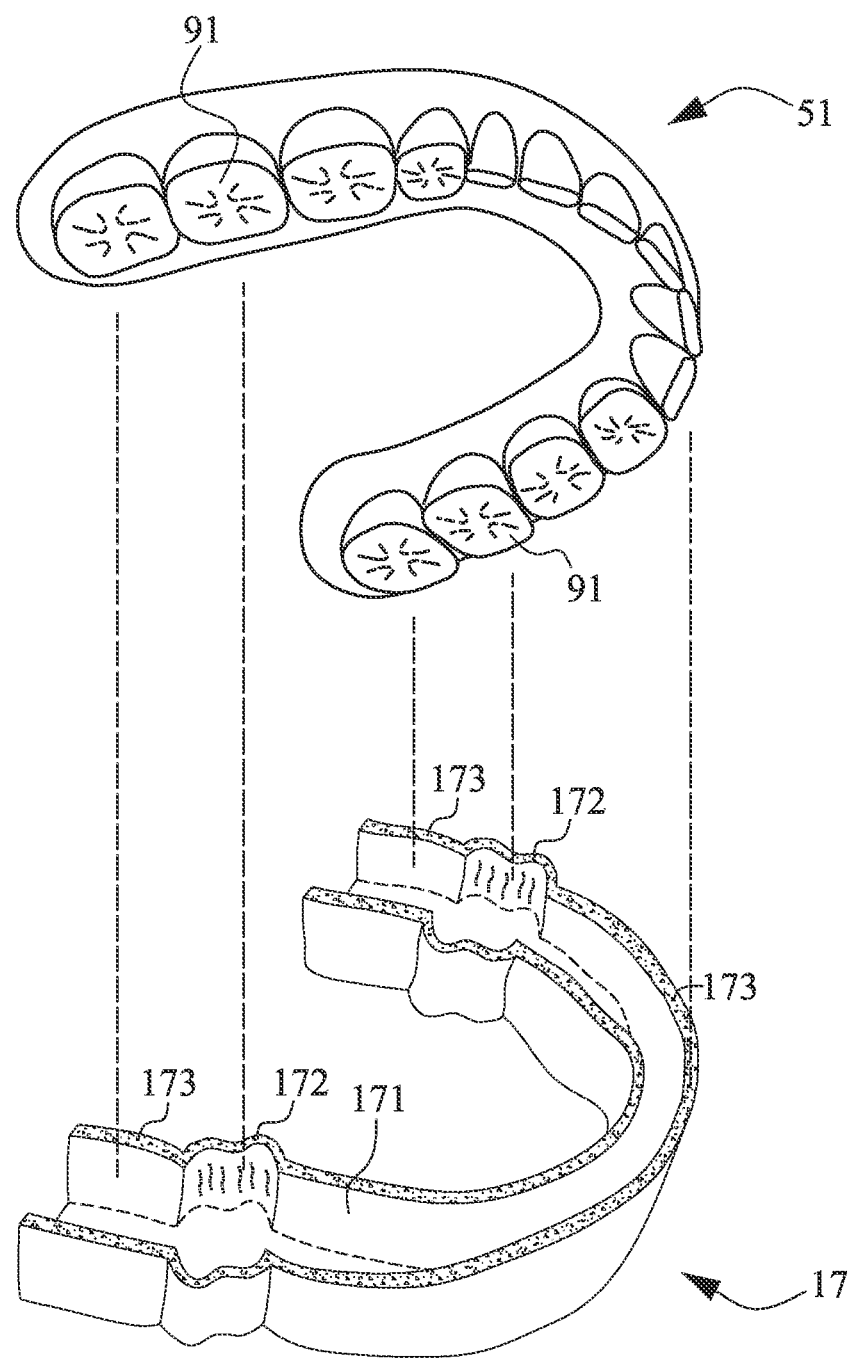
FIG. 9A is diagram demonstrating that the customized tooth site and the general tooth site of the orthodontic appliance match with teeth of the upper jaw cast according to the second embodiment of the present invention.
Figure 9B:
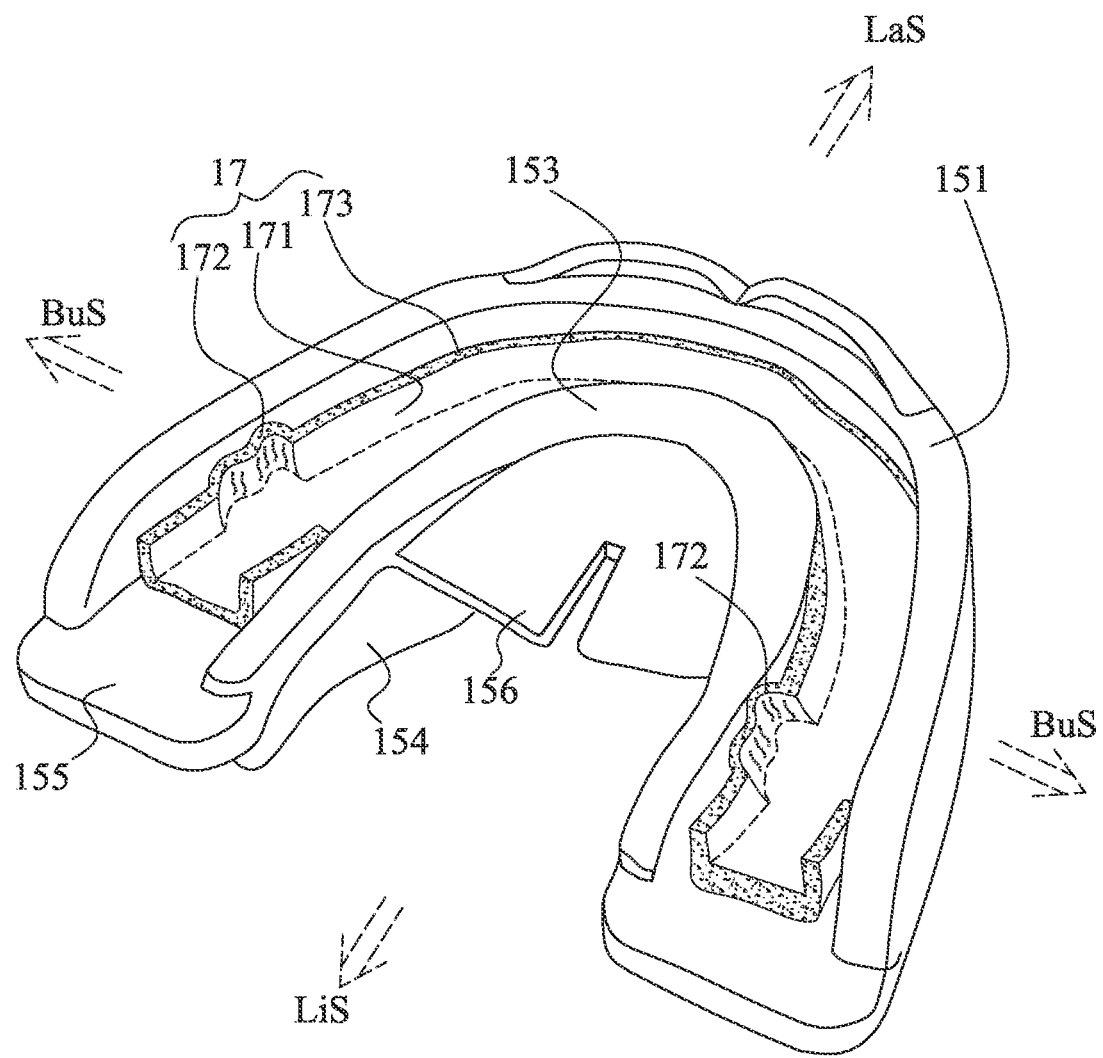
FIG. 9B is diagram of the customized tooth site and the general tooth site of the orthodontic appliance according to the second embodiment of the present invention.

There are some other embodiments. Please refer to FIG. 9A and FIG. 9B, the hard maxillary retainer 17 of the orthodontic appliance 1 has two customized teeth sites 172 and three general teeth sites 173. Since the upper jaw cast 51 and lower jaw cast 52 are duplicated through patient's mouth, the upper jaw cast 51 and the lower jaw cast 52 certainly have the first molars 91 disposed thereon. The customized teeth sites 172 can be fitted and detachably engaged with patient's first molar 91 of patient's maxillary dental arch. The general teeth sites 173 can accommodate patient's other teeth of the maxillary dental arch. Each customized tooth site 172 is connected to end of the general tooth site 173, so that the customized teeth sites 172 and the general teeth sites 173 can be formed into a curve-shaped dental arch. Seeing through the cross section view, the profile of the general teeth sites 173 are a U-shaped or V-shaped groove, which can cover and correspond to multiple teeth at the same time. The contour of the U-shaped groove or V-shaped groove of the general teeth sites 173 are inconsistent with the contour of patient's teeth. The profile of the general teeth sites 173 are universal, so there is no need to carry out customized design through dental software, and thus cost for structural design and investment of manpower are saved. The general tooth site 173 can cover several patient's teeth, in which these teeth have different sizes or different shapes. In this manner, the general teeth sites 173 will not be fully matched and engage with patient's teeth. It is noticed that the orthodontic appliance 1 of the second embodiment has high potential to treat children in age of 7~9. The orthodontic appliance 1 in this embodiment can be used for anchoring patient's first molar 91, to achieve function of occlusion guide; so that the patient in age 7~9 may let the maxillary and mandibular dental arch be arranged to meet Class I occlusion relationship according to the Angle's Classification. Besides, the orthodontic appliance 1 can also help maintain enough growth spaces for pre-molar (i.e., bicuspid). Similarly, the hard mandibular retainer 18 has two customized teeth sites 182 and at least one general tooth site. The customized teeth sites 182 can be fitted and detachably engaged with patient's first molar 91 of the mandibular dental arch. The general teeth sites can correspond to and accommodate patient's other teeth of the mandibular dental arch. Besides, the customized teeth sites 182 are also connected to end of the general tooth site as demonstrated in FIG. 2A, FIG. 3A and FIG. 8B. Furthermore, the orthodontic appliance 1 of the second embodiment can be fabricated in the steps addressed in FIG. 1A and FIG. 1B.

Third Embodiment

Figure 10A:
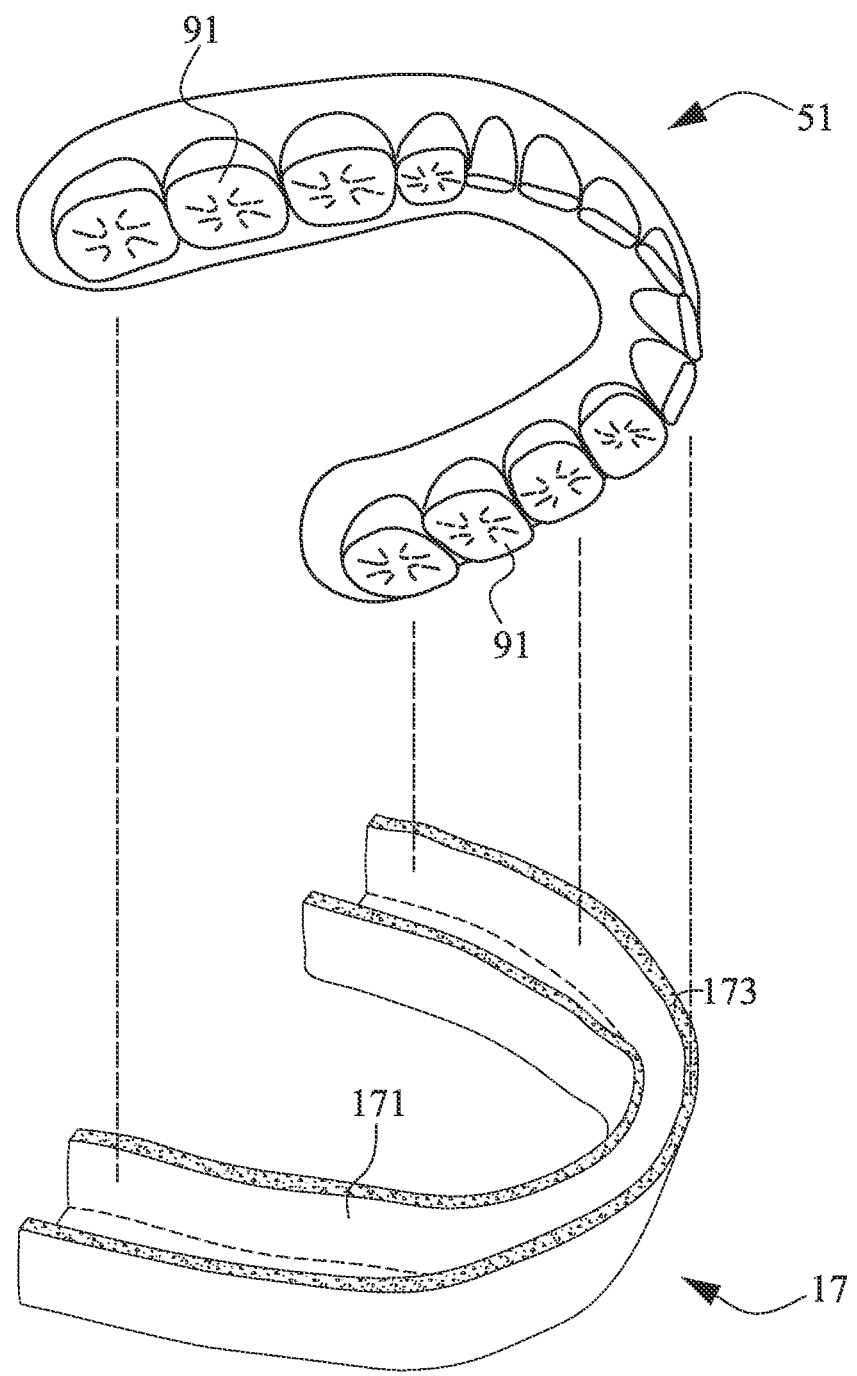
FIG. 10A is diagram demonstrating that the customized tooth site and the general tooth site of the orthodontic appliance match with teeth of the upper jaw cast according to the third embodiment of the present invention.
Figure 10B:
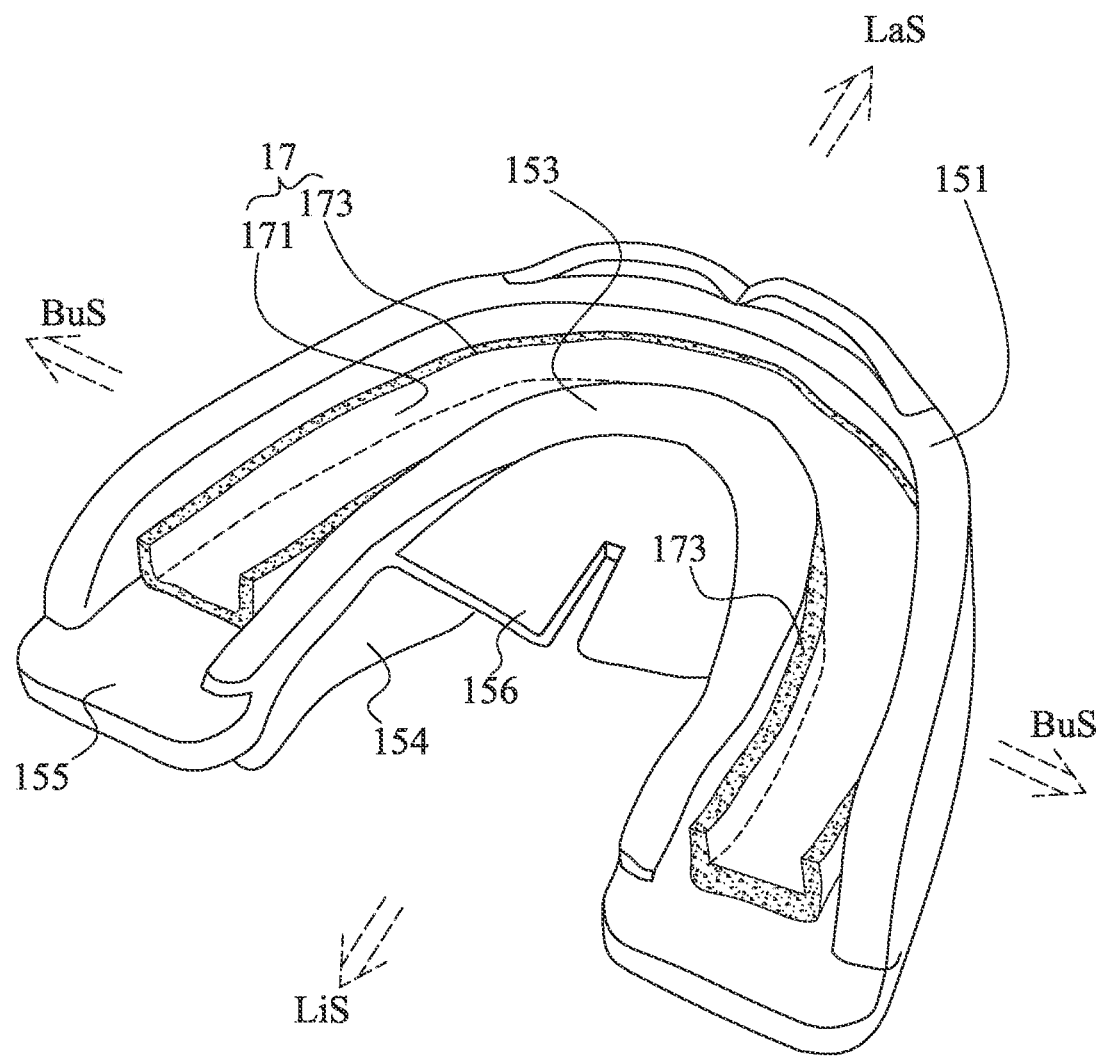
FIG. 10B is diagram of the customized tooth site and the general tooth site of the orthodontic appliance according to the third embodiment of the present invention.

Please refer to FIG. 10A and FIG. 10B, the orthodontic appliance 1 of the third embodiment has general tooth sites 173 disposed on the hard maxillary retainer 17, without customized tooth site 172, 182. The general tooth site (173) can cover and accommodate all teeth of patient's maxillary dental arch. Similarly, the hard mandibular retainer (18) has only a general tooth site covered and accommodated all teeth of patient's mandibular dental arch. It is noticed that the orthodontic appliance 1 of this embodiment has high potential to treat children in age of 5~7, because the dental patient in this age group is normally in the stage of deciduous teeth. Therefore, the hard maxillary retainer 17 can force the children grow and expand the maxillary dental arch through the general tooth site 173, and thus the maxillary dental arch can have enough space for subsequent eruption of permanent teeth, without teeth crowding. The orthodontic appliance 1 of the third embodiment may also be applicable for fabricating steps addressed in FIG. 1A and FIG. 1B.

As aforementioned addressed, the orthodontic appliance 1 of these three embodiments can treat the dental patients who suffer muscle dysfunction or have problems such as dysphagia with tongue prick or reverse swallowing. Moreover, the soft retainer 15 of the orthodontic appliance 1 can improve patient's insufficiency of chewing or unilateral mastication through the occlusal training. Since the 1990, it is found that there are dental bone forming cells (i.e., osteoblast) and bone resorption cells (i.e., osteoclast) in the alveolar bone, which affect the growth or contraction of human's the upper and lower jaw. When dental patient uses the orthodontic appliance 1 of the present invention, it can stimulate patient's oral sensitive cells through occlusion of upper jaw and lower jaw, and then convert the occlusal force into biological nerve signals of human body, to activate the "bone forming cells" or "bone resorption cells"; therefore, alveolar bone growth or resorption is thus controllable. In this manner, human's alveolar bone may react to the designated contour of the orthodontic appliance 1, to activate osteoblast or osteoclast cells, and afterward grow or contract alveolar bone to shape the chin contour when orthodontic treatment is made. Thus, correction for jawbone, mandibular bone growth or chin shaping is achievable. In words, orthodontic treatment through the present invention can take advantage of tissue change biology to treat overdevelopment of dental arch or insufficient alveolar bone, and further have functions such as alveolar bone shaping, bone repair, bone correction and teeth arrangement.

Fourth Embodiment

Figure 11:
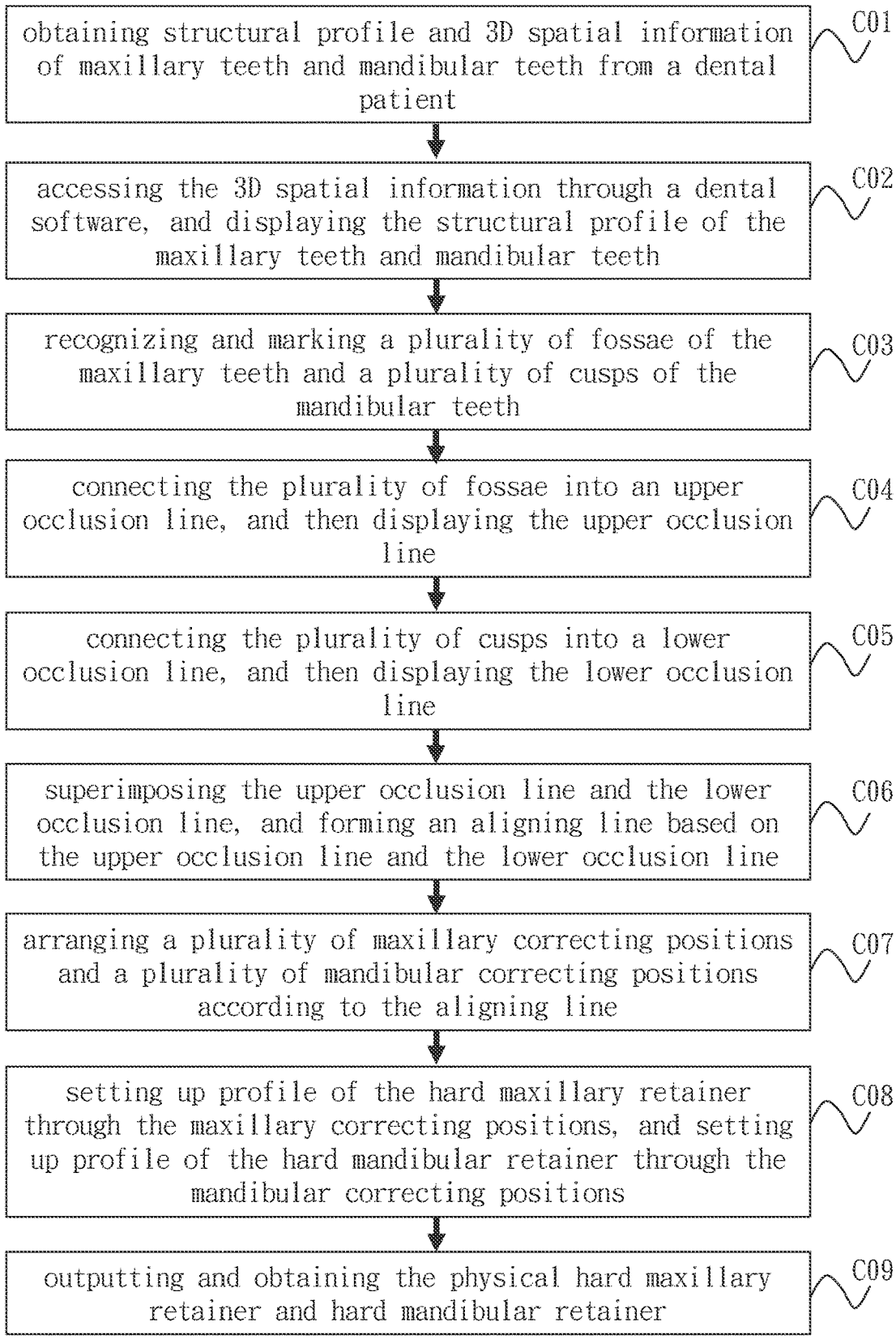
FIG. 11 is flow chart of manufacturing method of the orthodontic appliance according to the fourth embodiment of the present invention.
Figure 12:
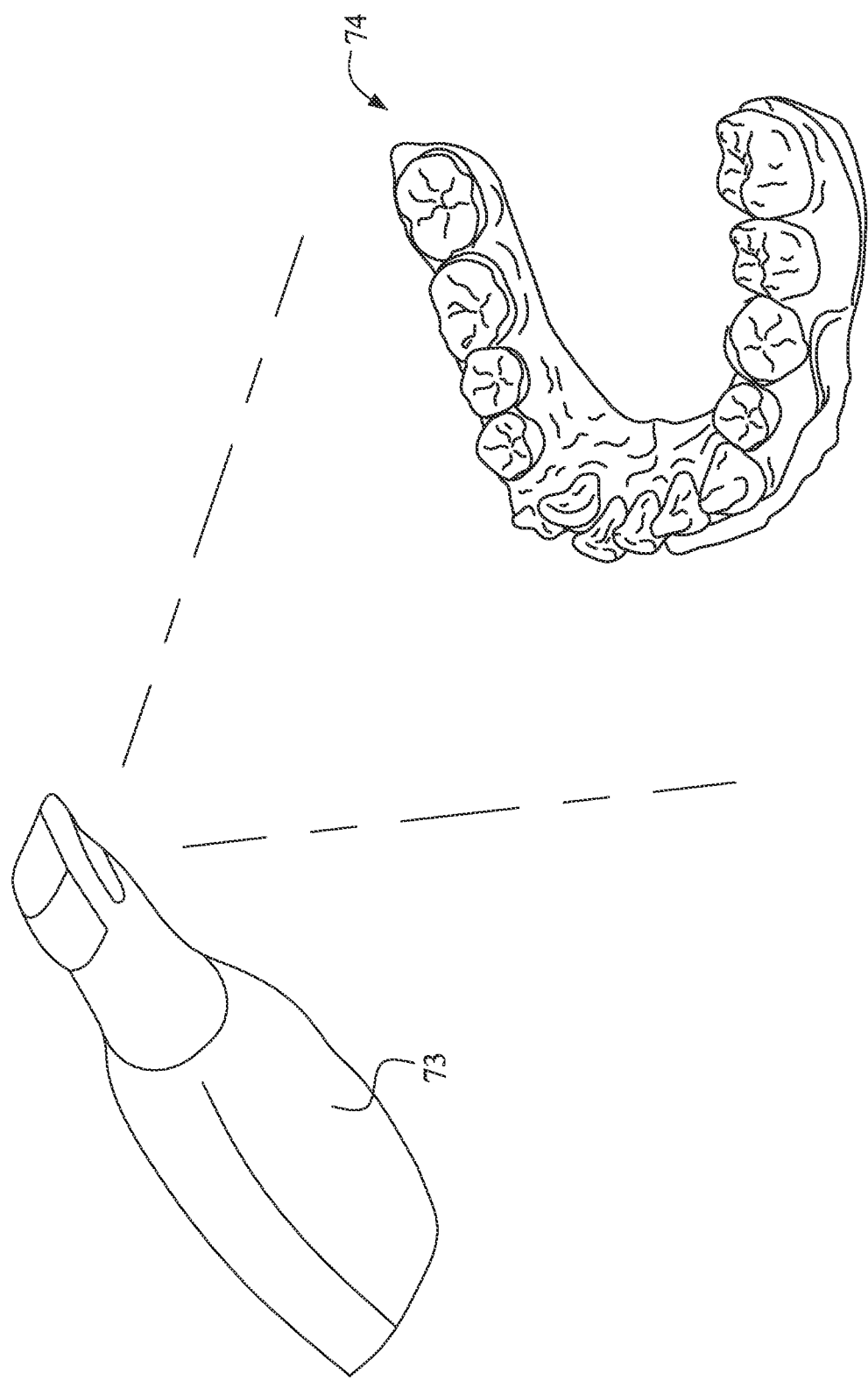
FIG. 12~20 are diagrams demonstrating the manufacturing method of orthodontic appliance according to the fourth embodiment of the present invention.
Figure 13:
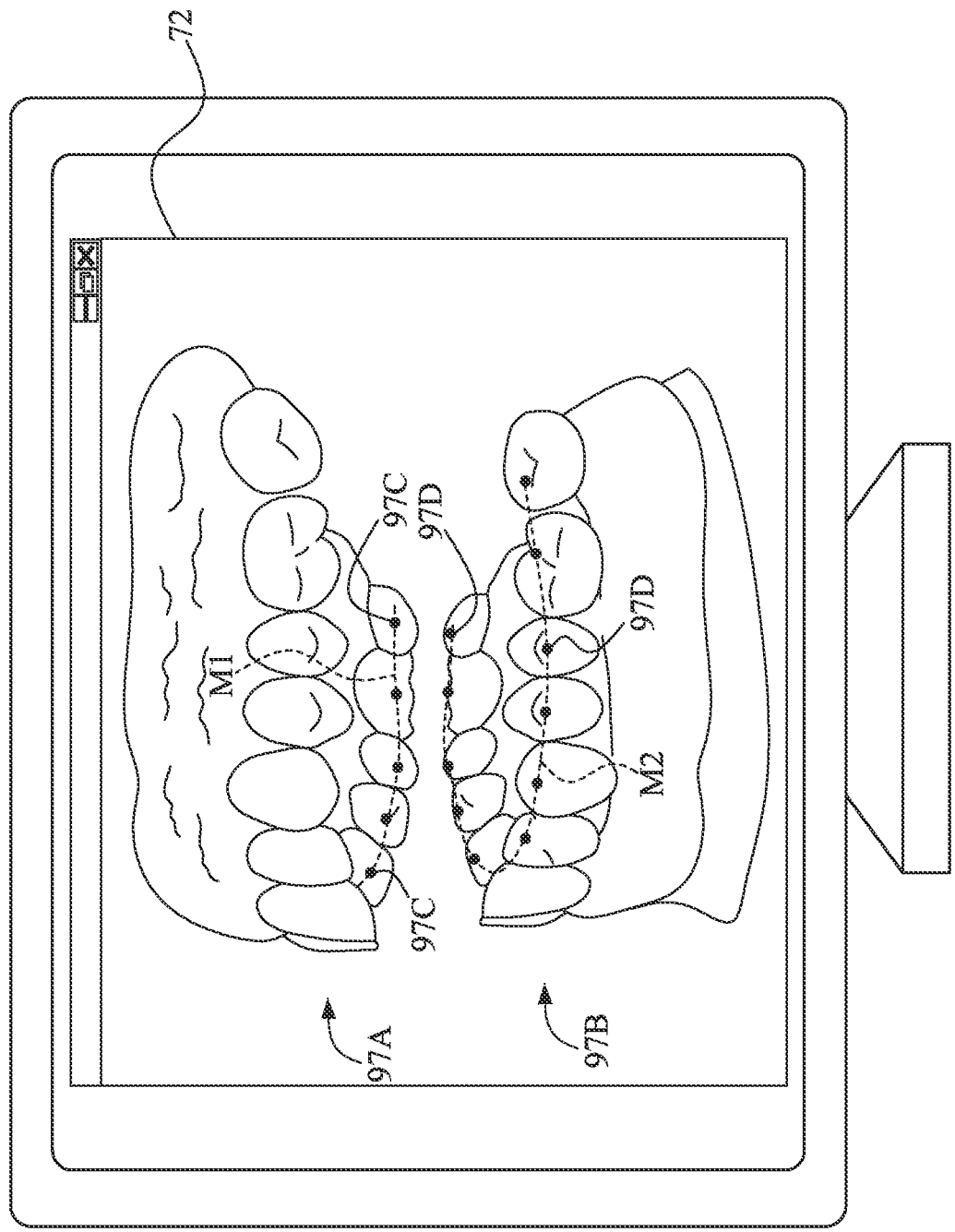
Figure 14:
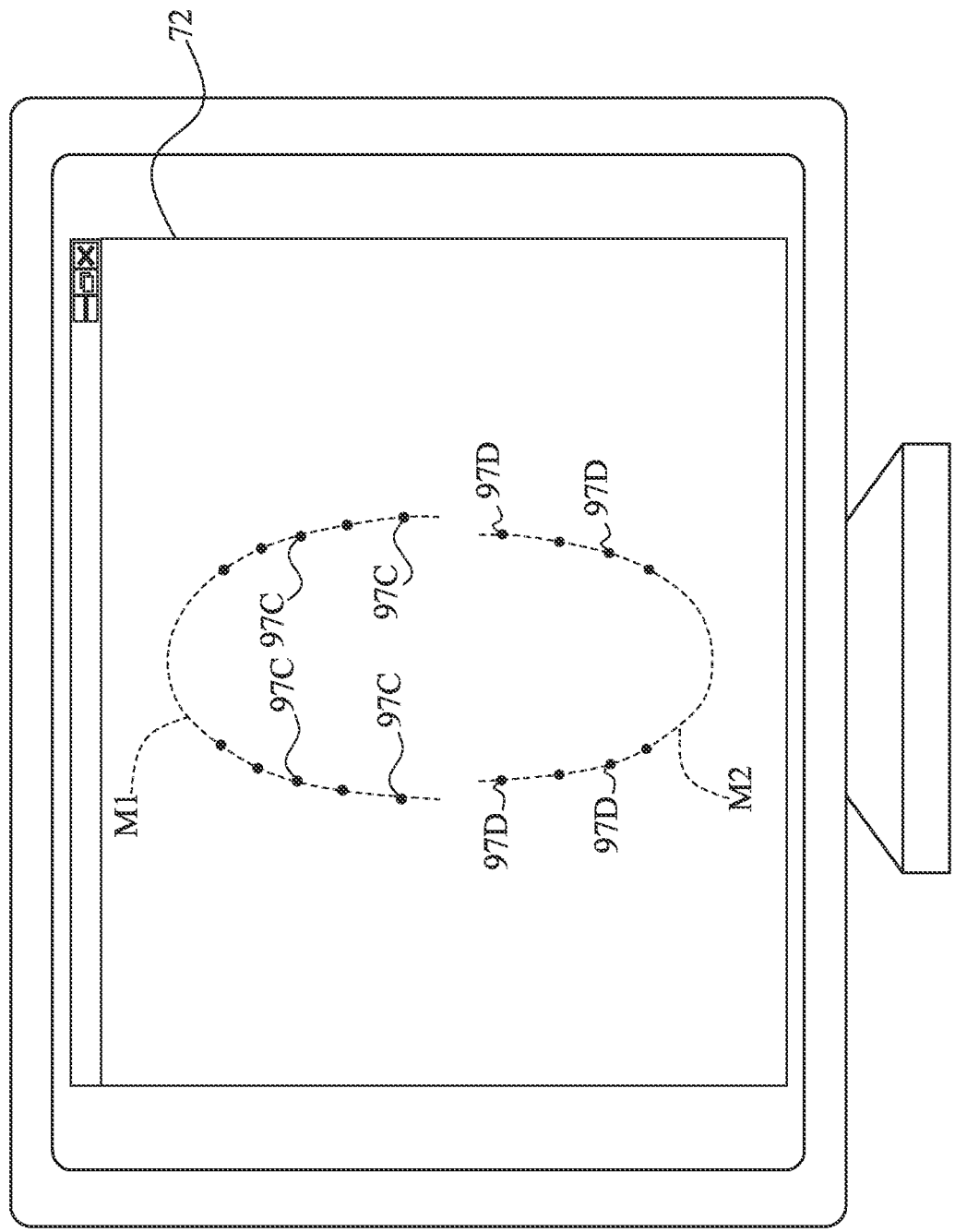
Figure 15:
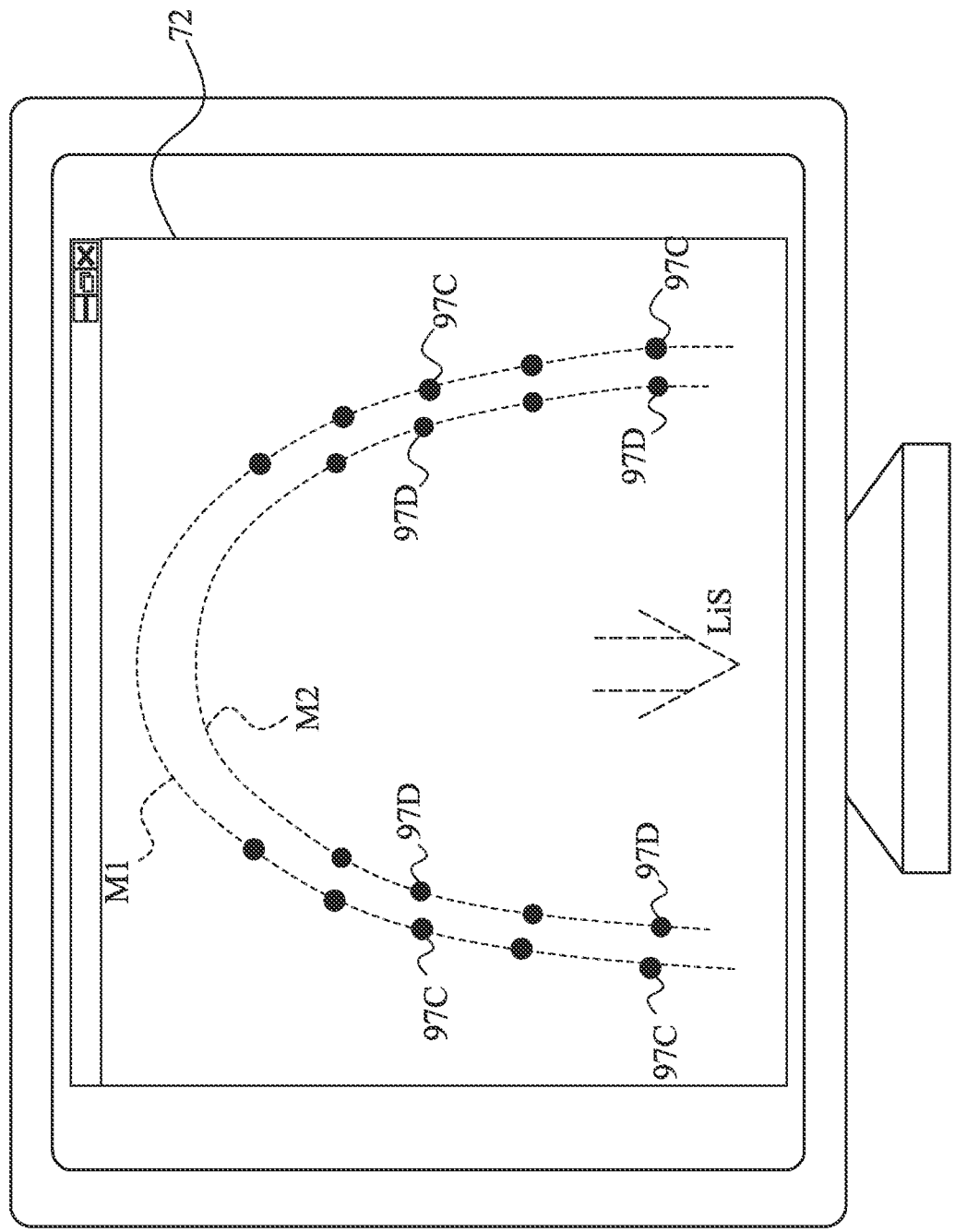
Figure 16:
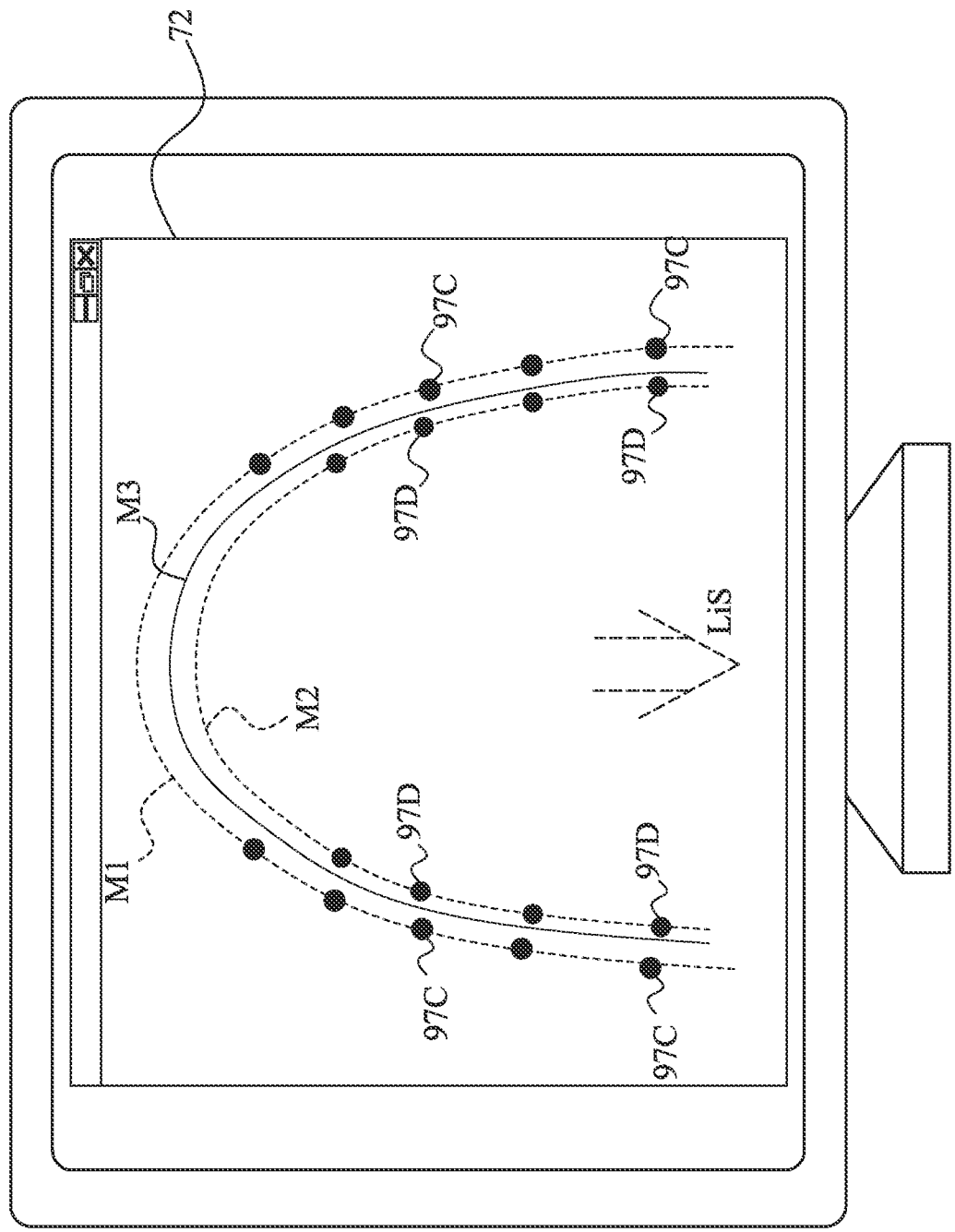
Figure 17:
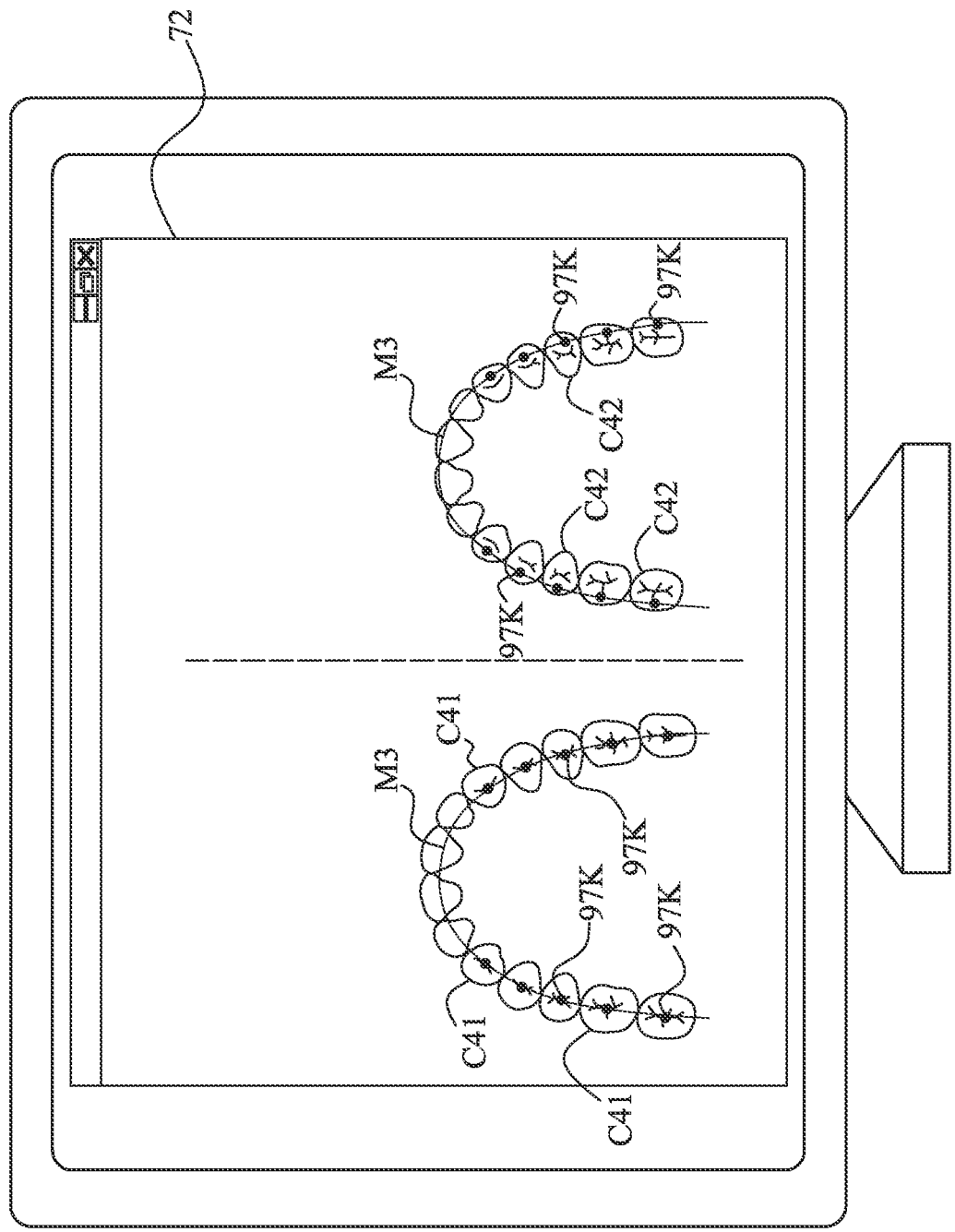

The present invention further suggests the fourth embodiment to show the manufacturing method of the hard maxillary retainer 17 and hard mandibular retainer 18, so that the hard maxillary retainer 17 and hard mandibular retainer 18 can perfectly meet and engage with patient's upper jaw and lower jaw. Please refer to FIG. 11, FIG. 11 is flow chart of manufacturing method of the orthodontic appliance according to the fourth embodiment of the present invention. As shown in FIG. 11, the fabrication of the hard maxillary retainer 17 and the hard mandibular retainer 18 has the following sub-steps: obtaining structural profile and 3D spatial information of maxillary teeth 97A and mandibular teeth 97B from a dental patient (Step C01). Specifically, the profiles of the maxillary teeth 97A and mandibular teeth 97B can be obtained through scanning the patient's oral cavity or a plaster dental mold 74, by means of a scanning device 73 demonstrated in FIG. 12; the plaster dental mold 74 is generally pre-fabricated through replicating dental patient's oral cavity. As shown in FIG. 13, the dentist or dental technician can access the 3D spatial information of the maxillary teeth 97A and mandibular teeth 97B through a dental software 72, and then the structural profile of the maxillary teeth 97A and mandibular teeth 97B are able to be displayed in the dental software 72 (Step C02). As a result, a plurality of fossae 97C of the maxillary teeth 97A and a plurality of cusps 97D of the mandibular teeth 97B are recognized and marked (Step C03); afterward, the plurality of fossae 97C can be connected into an upper occlusion line M1, and then the upper occlusion line M1 is displayed (Step C04). Similarly, the plurality of cusps 97D can be connected into a lower occlusion line M2, and then the lower occlusion line M2 is displayed (Step C05). As shown in FIG. 14 and FIG. 15, the upper occlusion line M1 and lower occlusion line M2 can be superimposed, arranged, or set side by side to compare with each other, thus the dentist or dental technician can detect the occlusal deviation through the dental software 72. Afterward as shown in FIG. 16, the upper occlusion line M1 and the lower occlusion line M2 are superimposed, to form an aligning line M3 based on the upper occlusion line M1 and the lower occlusion line M2 (Step C06). The aligning line M3 is located between the upper occlusion line M1 and the lower occlusion line M2, in this manner, the teeth positions of aligning line M3 are located between the teeth positions of the upper occlusion line M1 and the teeth positions of the lower occlusion line M2. To determine each site of the aligning line M3, the dentist or dental technician can adjust the proportion of how much the site close to the upper occlusion line M1 or lower occlusion line M2 along with the lingual side LiS orientation; the proportion is a parameter which can be set and arranged, and then inputted through the dental software 72. Clinically the parameter of the proportion can be preferably scale ratio of occlusion line M1 or M2. Namely the dentist or dental technician can input the parameter of scale ratio to determine the exact position of each point of the aligning line M3, and to let the aligning line M3 locate between the upper occlusion line M1 and lower occlusion line M2. When the aligning line M3 is determined, as shown in FIG. 17, the matching points 97K of Cusp-to-Fossa are thus formed on the aligning line M3 to demonstrate right occlusal relationship between the cusps 97D of the mandibular teeth 97B and the fossae 97C of the maxillary teeth 97A. As further shown in left half screen of the dental software 72 in the FIG. 17, the pluralities of matching points 97K will correspond to patient's corrected fossae 97C of the maxillary teeth 97A, in which the corresponding condition is further shown in FIG. 21~23. As a result, pluralities of maxillary correcting positions C41 can be obtained based on each site of aligning line M3 Similarly, as shown in right half screen of the dental software 72 in the FIG. 17, the pluralities of matching points 97K will also correspond to patient's corrected cusps 97D of the mandibular teeth 97B, in which the corresponding condition is further shown in FIG. 21~23. Subsequently pluralities of mandibular correcting positions C42 are also obtained based on each site of aligning line M3. Namely the matching points 97K can meet expected sites (i.e., the sites where patient's teeth are expected to move to) of maxillary teeth 97A and mandibular teeth 97B. Hence the maxillary teeth 97A and the mandibular teeth 97B will be moved to the maxillary correcting positions C41 and mandibular correcting positions C42 after orthodontic process is made. In this manner the maxillary teeth 97A and mandibular teeth 97B will achieve Maximal Intercuspation Position and meet the best Cusp to Fossa Relationship, and thus the maxillary teeth 97A and mandibular teeth 97B are able to move toward the matching points 97K, to meet Class I occlusion relationship of Angle's Classification. By means of the arrangement of teeth positions in the dental software 72 addressed, each of maxillary teeth 97A and mandibular teeth 97B can be guided and corrected toward the expected maxillary correcting positions C41 and mandibular correcting positions C42, to fulfill Centric Occlusion (CO) state, and thus patient's upper jaw and lower jaw can achieve Maximum Intercuspation relationship.

Figure 18:
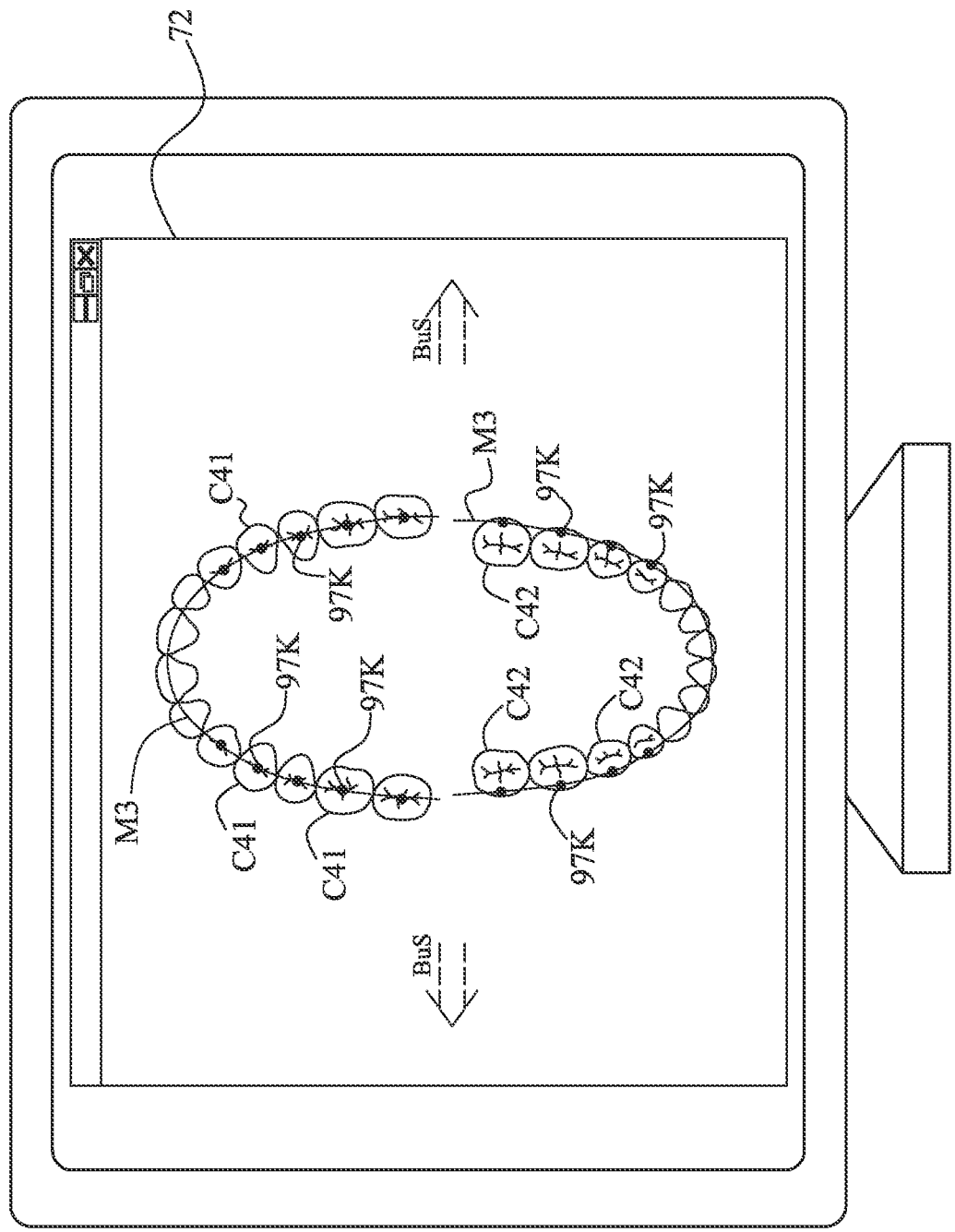
Figure 19:
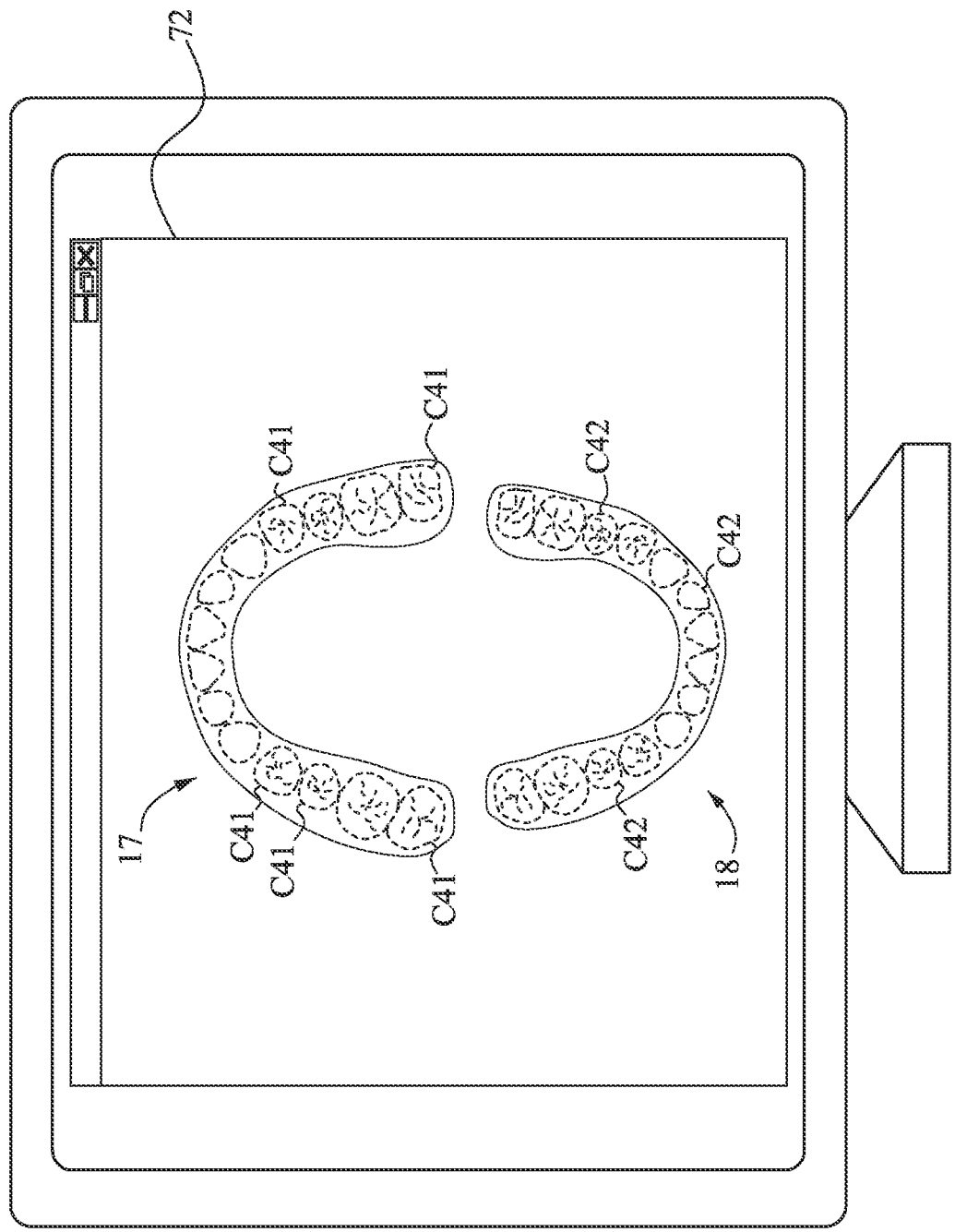
Figure 20:
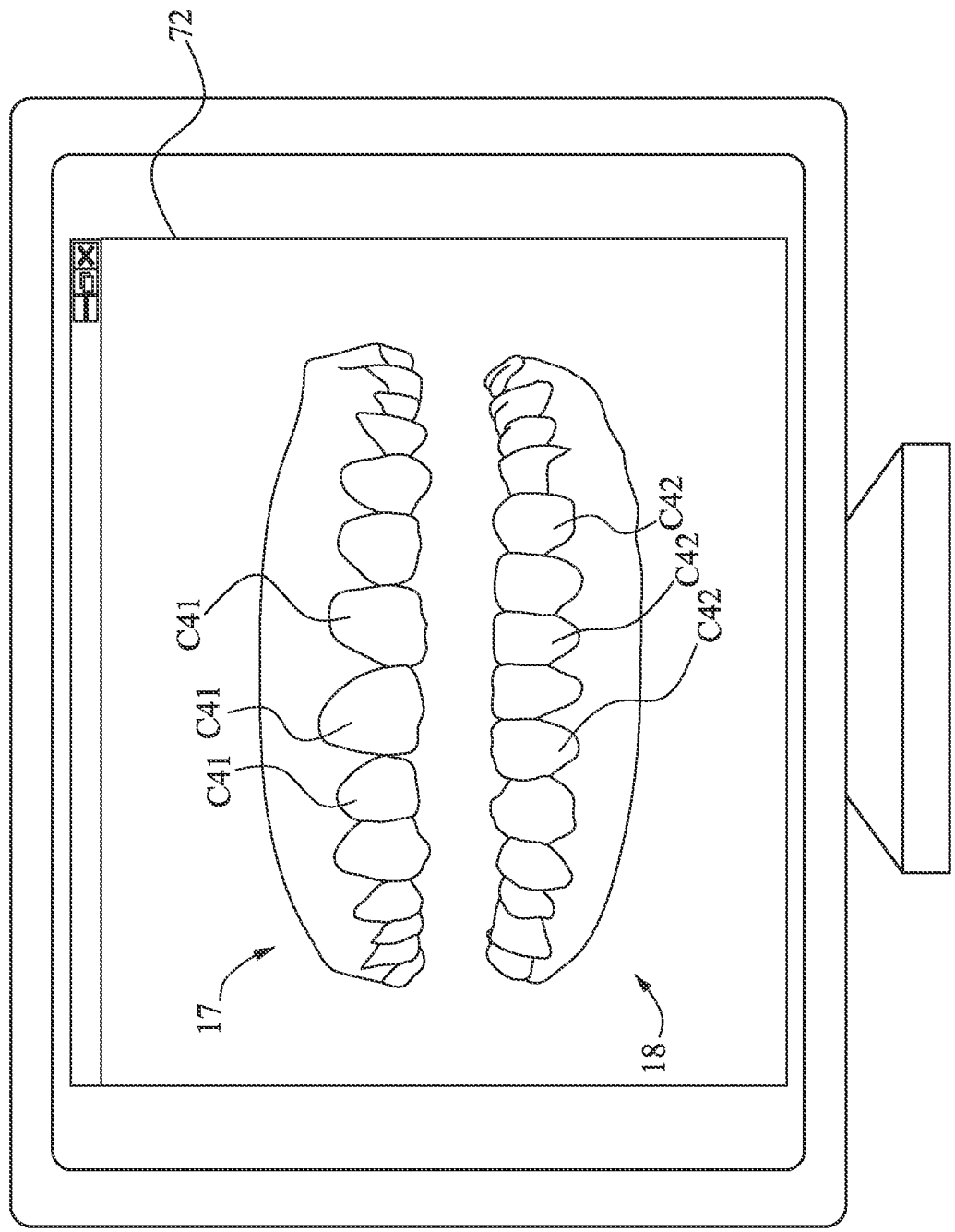
Figure 21:
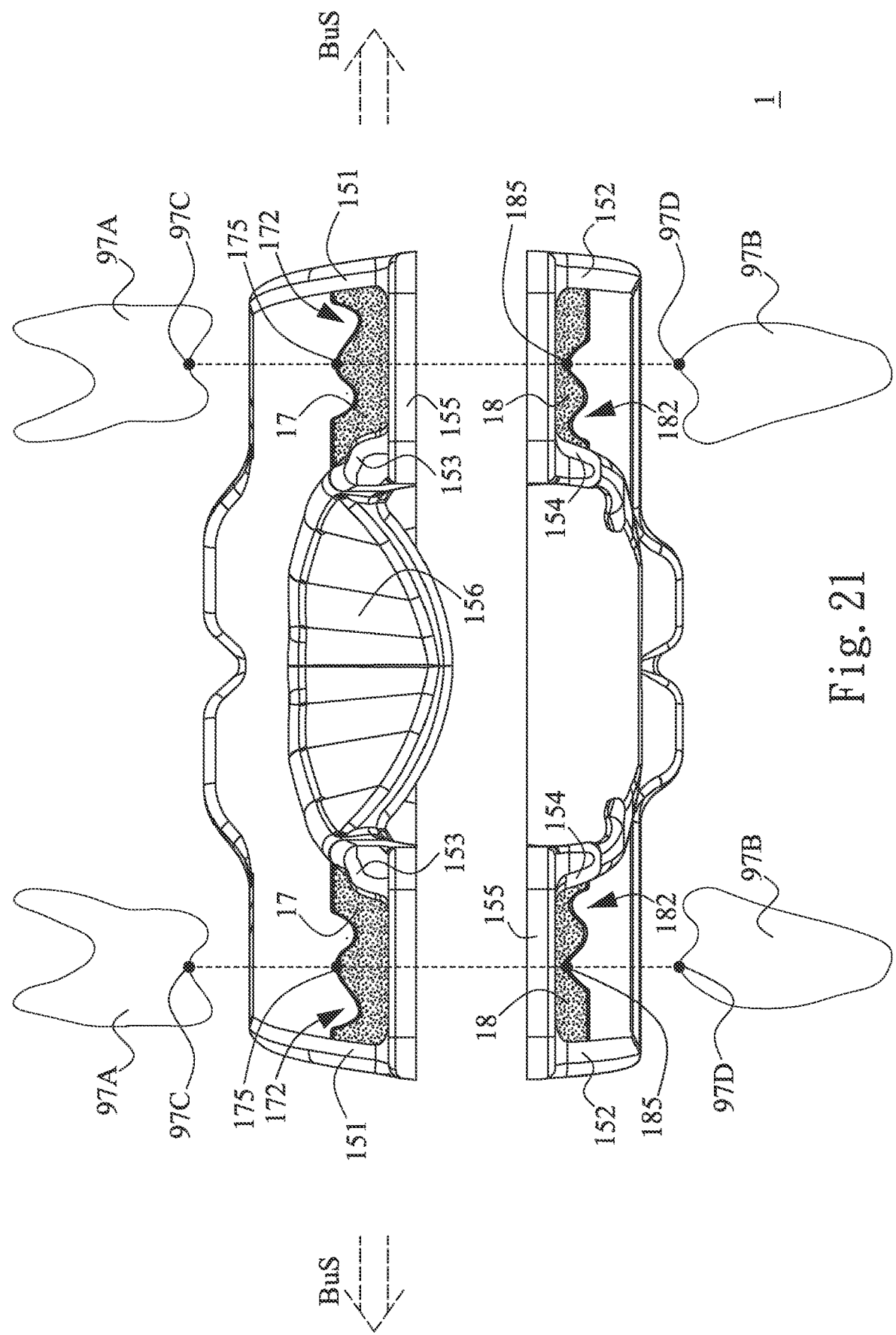
FIG. 21 is diagram demonstrating that maxillary teeth, mandibular teeth correspond to hard maxillary retainer and hard mandibular retainer.

As further shown in FIG. 18, the pluralities of maxillary correcting positions C41 and mandibular correcting positions C42 are arranged according to each point of the aligning line M3 (Step C07). Afterward, profile of the hard maxillary retainer 17 is then set up by means of the maxillary correcting positions C41, and profile of the hard mandibular retainer 18 is set up by means of the mandibular correcting positions C42 (Step C08). Digital profile of hard maxillary retainer 17 and hard mandibular retainer 18 generated in the dental software 72 is demonstrated in FIG. 19. Lastly as shown in FIG. 20, the physical hard maxillary retainer 17 and hard mandibular retainer 18 are outputted and obtained (Step C09), thus the hard maxillary retainer 17 and hard mandibular retainer 18 can be provided to the Step A01 of FIG. 1A and then integrated into the orthodontic appliance 1 as demonstrated in FIG. 8A~8C. Namely profile of the hard maxillary retainer 17 and hard mandibular retainer 18 are designed in the dental software 72, and afterward fabricated. Favorably, the hard maxillary retainer 17 and hard mandibular retainer 18 can be outputted and obtained through 3D printing or plastic inject molding. When dental patient bites the orthodontic appliance 1 as shown in FIG. 21, the customized tooth site 172 (corresponded to the maxillary correcting position C41 in dental software 72) of the hard maxillary retainer 17 will be corresponded to patient's maxillary teeth 97A, and the customized tooth site 182 (corresponded to the mandibular correcting position C42 in dental software 72) of the hard mandibular retainer 18 will be corresponded to patient's mandibular teeth 97B. Therefore, the maxillary correcting positions C41 and mandibular correcting positions C42 are designated to make the customized teeth sites 172 and 182 have function of guiding and correcting teeth, so that teeth deviation, dislocation, malocclusion, or teeth unmatch can be treated. Additionally, in another embodiment, the hard maxillary retainer 17 and the hard mandibular retainer 18 can also solely utilized to treat teeth deviation, dislocation, malocclusion, and teeth unmatch, no need to integrate with the soft retainer 15 and the orthodontic appliance 1.

In the further embodiment, the following sub-step can be carried out after Step C04 or Step C05: segmentally adjusting profile of the upper occlusion line M1, lower occlusion line M2 or aligning line M3 toward direction of dental midline, or selectively adjusting the orientation or position of specific point of maxillary correcting positions C41 or mandibular correcting positions C42. Clinically change of aligning line M3 may influence face profile of dental patient, in this manner dentist or dental technician may also slightly move specific point of aligning line M3 to reshape patient's chin profile.

Figure 22:
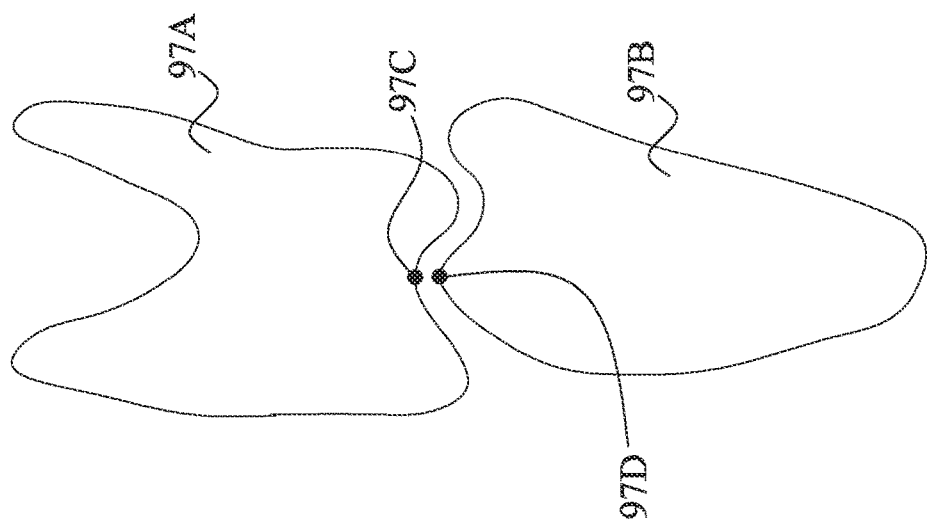
FIG. 22 is diagram demonstrating Cusp-to-Fossa Occlusal Relationship to maxillary teeth and mandibular teeth.

When the hard maxillary retainer 17 and the hard mandibular retainer 18 are fabricated and afterward bitted by dental patient, as shown in FIG. 21, patient's maxillary teeth 97A will be guided and forced to engage with the customized teeth sites 172, and the mandibular teeth 97B will be guided and forced to engage with the customized teeth sites 172. In this manner, the hard maxillary retainer 17 may move, rotate and then correct each maxillary tooth 97A; similarly the hard mandibular retainer 18 may move, rotate and then correct each mandibular tooth 97B. More specifically, the customized tooth site 172 has a first corresponding point 175, and the customized tooth site 182 has a second corresponding point 185. The first corresponding point 175 of the customized tooth site 172 can be corresponded to and directly close to the fossa 97C of the maxillary tooth 97A above; similarly the second corresponding point 185 of the customized tooth site 182 can be corresponded to and directly close to the cusp 97D of the mandibular tooth 97B. After dental correction treatment through the orthodontic appliance 1, the fossa 97C of the maxillary tooth 97A will correspond to the cusp 97D of the mandibular tooth 97B, and so that the maxillary teeth 97A and mandibular teeth 97B will have maximum contact area, to achieve Cusp-to-Fossa Occlusal Relationship. The best result after orthodontic treatment is shown in FIG. 22, in which the fossae 97C of maxillary teeth 97A can be corresponded to and close to the cusps 97D of mandibular teeth 97B; therefore, patient's maxillary teeth 97A and mandibular teeth 97B can meet Cusp-to-Fossa Occlusal Relationship, to keep the occlusion pressure spread and dispersed. In this manner, excessive local pressure or too much stress concentration on the teeth will not be happened. Furthermore, the maxillary teeth 97A and mandibular teeth 97B will thus be putted in Maximum Intercuspal Position (MIP). Therefore, it can reduce the chance of bad occlusal contact, temporomandibular joint disorder, and joint inflammation, and hence the muscles which control jaw movement will become more relaxed and comfortable. Therefore, it is critical to achieve Cusp-to-Fossa Occlusal Relationship between the maxillary teeth 97A and mandibular teeth 97B.

Figure 23:
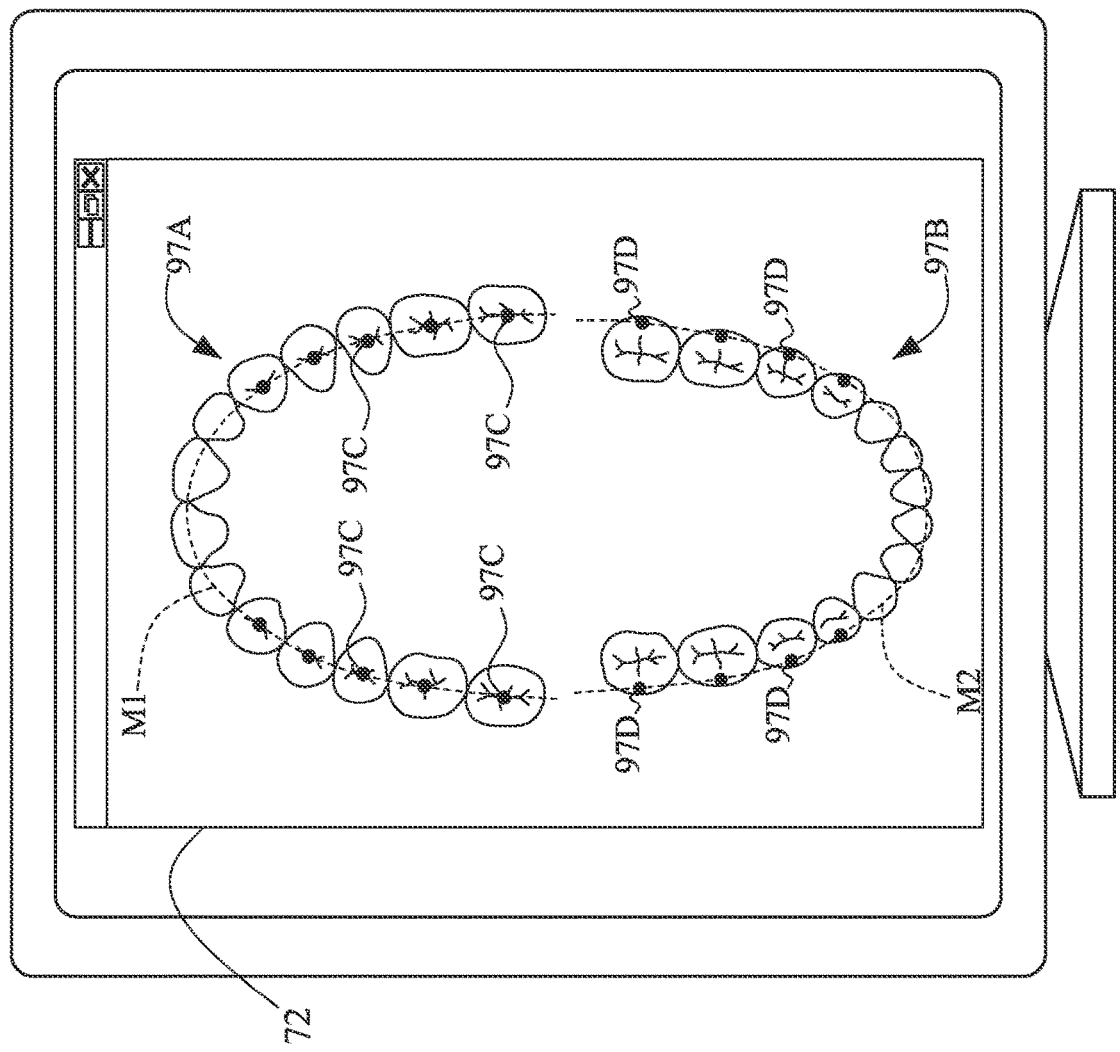
FIG. 23 is diagram demonstrating occlusion line of maxillary teeth and mandibular teeth in the dental software.

Please refer to FIG. 23, FIG. 23 is diagram demonstrating occlusion line of maxillary teeth and mandibular teeth in the dental software. As shown in FIG. 23, each of the fossae 97C of the maxillary teeth 97A will be corresponded to each of the cusps 97D of the mandibular teeth 97B. The pluralities of fossae 97C are connected and formed into the curved upper occlusion line M1, and the pluralities of the cusps 97D are also connected and formed into the curved lower occlusion line M2. Noted that the fossa 97C is located at center of each maxillary tooth 97A, therefore the pluralities of the fossae 97C formed into the upper occlusion line M1 are normally called "Maxillary Central Line". If the upper occlusion line M1 coincides with the lower occlusion line M2, the expecting Cusp-to-Fossa Occlusal Relationship is achieved, namely the best condition of orthodontic treatment is made. To ensure the treatment result, the dentist or dental technician may arrange and adjust the maxillary correcting positions C41 and mandibular correcting positions C42, or slightly move and rotate each point of the aligning line M3 through the dental software 72. In this manner, the exact locations of customized teeth sites 172 and the customized teeth sites 182 with respect to the hard maxillary retainer 17 and hard mandibular retainer 18 are thus made.

Finally, the orthodontic appliance 1 and its manufacturing method thereof have hard maxillary retainer 17 and the hard mandibular retainer 18, played the role of "invisible braces", to treat cross arrangement, dislocation, reverse location, or skewed arrangement of teeth, and even make the maxillary dental arch and the mandibular dental arch arrange in order and align in a beautiful, curved shape. Besides, the orthodontic appliance 1 of present invention may be customized manufactured according to patient's growing curve, age, or teeth condition. If the patient is during permanent teeth eruption period, the orthodontic appliance 1 can further help patient grow the jawbone and rearrange profile of dental arch, so that dental surgery for alveolar growth deformity or orthodontic treatment for abnormal occlusion are not required. The orthodontic appliance 1 uses hard material, i.e., hard maxillary retainer 17 and hard mandibular retainer 18, to provide greater mechanical force on pushing patient's teeth, therefore the time for orthodontic process is shortened. Noticed that orthodontic appliance 1 utilizing hard material may have advantage of preventing the structure from bitten and worn by teeth. The orthodontic appliance 1 utilizes soft retainer 15 to correct occlusion of patient's maxillary dental arch and mandibular dental arch, to make the dental arches meet Class I occlusion relationship according to the Angle's Classification and make patient's upper jaw and lower jaw move to Centric Relation (CR). In this manner, stability of occlusion is thus improved. The soft retainer 15 may further have advantages of stimulating bone forming cells or bone resorption cells, to control alveolar bone growth or resorption, and reshape patient's alveolar bone. Moreover, the soft retainer 15 have advantage of reducing and eliminating symptom of "mouth breathing" caused by snoring and lowered tongue position; thus, the orthodontic appliance 1 can have breath-training functions for the patient who suffered sleep apnea or severe snoring, to reduce the snoring noise and frequency, and improve his/her sleep quality. In this manner, the orthodontic appliance 1 having both hard and soft materials (hard maxillary retainer 17, hard mandibular retainer 18 and soft retainer 15) may combine those benefits addressed before, and hence have huge potential in dental clinic.

The figures and descriptions supra set forth illustrated the preferred embodiments of the instant disclosure; however, the characteristics of the instant disclosure are by no means restricted thereto. All changes, alternations, combination, or modifications conveniently considered by those skilled in the art are deemed to be encompassed within the scope of the instant disclosure delineated by the following claims.

What is claimed is:

1. A manufacturing method for orthodontic appliance (1), the orthodontic appliance (1) having a maxillary retainer (17) and a mandibular retainer (18), the manufacturing method comprising:

Step C01: obtaining structural profile and 3D spatial information of maxillary teeth (97A) and mandibular teeth (97B) from a dental patient;

Step C02: accessing the 3D spatial information through a dental software (72), and displaying the structural profile of the maxillary teeth (97A) and mandibular teeth (97B);

Step C03: recognizing and marking a plurality of fossae (97C) of the maxillary teeth (97A) and a plurality of cusps (97D) of the mandibular teeth (97B);

Step C04: connecting the plurality of fossae (97C) into an upper occlusion line (M1), and then displaying the upper occlusion line (M1);

Step C05: connecting the plurality of cusps (97D) into a lower occlusion line (M2), and then displaying the lower occlusion line (M2);

Step C06: superimposing the upper occlusion line (M1) and the lower occlusion line (M2), and forming an aligning line (M3) based on the upper occlusion line (M1) and the lower occlusion line (M2), wherein the aligning line (M3) is located between the upper occlusion line (M1) and the lower occlusion line (M2);

Step C07: arranging a plurality of maxillary correcting positions (C41) and a plurality of mandibular correcting positions (C42) according to the aligning line (M3);

Step C08: setting up profile of the maxillary retainer (17) through the maxillary correcting positions (C41), and setting up profile of the mandibular retainer (18) through the mandibular correcting positions (C42); and Step C09: outputting and obtaining the physical maxillary retainer (17), the mandibular retainer (18) or the orthodontic appliance (1).

2. The manufacturing method for orthodontic appliance (1) according to claim 1, further having the following step: segmentally adjusting profile of the upper occlusion line (M1), lower occlusion line (M2) or aligning line (M3) toward direction of dental midline.

3. The manufacturing method for orthodontic appliance (1) according to claim 1, further having the following steps:

Step B03: utilizing the dental software (72) to calculate and simulate the shifting distance or rotating angle of each tooth;

Step B04: confirming the shifting distance or rotating angle of the teeth in whole orthodontic process, and modifying the profile of the maxillary retainer (17) and the mandibular retainer (18).

* * * * *